United States Patent
Choi et al.

(10) Patent No.: US 11,596,371 B2
(45) Date of Patent: Mar. 7, 2023

(54) TOMOGRAPHIC IMAGE PROCESSING APPARATUS AND METHOD OF SEPARATING MATERIAL OF OBJECT IN SPECTRAL TOMOGRAPHIC IMAGE, AND COMPUTER PROGRAM PRODUCT

(71) Applicant: Samsung Electronics Co., Ltd., Suwon-si (KR)

(72) Inventors: Yuna Choi, Suwon-si (KR); Changlae Lee, Suwon-si (KR); Jiyoung Choi, Suwon-si (KR); Jinwook Jung, Suwon-si (KR); Keyjo Hong, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 511 days.

(21) Appl. No.: 16/692,635

(22) Filed: Nov. 22, 2019

(65) Prior Publication Data

US 2020/0163637 A1 May 28, 2020

(30) Foreign Application Priority Data

Nov. 23, 2018 (KR) .................... 10-2018-0146774

(51) Int. Cl.
*G06T 7/00* (2017.01)
*A61B 6/00* (2006.01)
*A61B 6/03* (2006.01)

(52) U.S. Cl.
CPC .............. *A61B 6/463* (2013.01); *A61B 6/032* (2013.01); *A61B 6/461* (2013.01); *A61B 6/501* (2013.01);
(Continued)

(58) Field of Classification Search
CPC ......... A61B 6/463; A61B 6/032; A61B 6/461; A61B 6/501; A61B 6/5205; A61B 6/583;
(Continued)

(56) References Cited

U.S. PATENT DOCUMENTS 9,808,216 B2 11/2017 Schmidt et al.
2012/0114206 A1 5/2012 Avinash et al.
(Continued)

FOREIGN PATENT DOCUMENTS

WO 2018/098118 5/2018

OTHER PUBLICATIONS

Yanye Lu et al. "Material Decomposition Using Ensemble Learning for Spectral X-ray Imaging," IEEE Transactions on Radiation and Plasma Medical Sciences, vol. 2, No. 3, May 2018.
(Continued)

*Primary Examiner* — Siamak Harandi
(74) *Attorney, Agent, or Firm* — Staas & Halsey LLP

(57) ABSTRACT

A tomographic image processing apparatus including a display, an input interface configured to receive an external input, a storage storing an input tomographic image of an object, and at least one processor configured to control the display to display the input tomographic image, determine a material combination to be separated from the input tomographic image, and control the display to display material separation information corresponding to the determined material combination for a region of interest selected in the input tomographic image based on the external input. The input tomographic image is a spectral tomographic image having a plurality of tomographic images respectively corresponding to a plurality of energy levels.

18 Claims, 27 Drawing Sheets

(52) U.S. Cl.
CPC ............ *A61B 6/5205* (2013.01); *A61B 6/583* (2013.01); *G06T 7/0012* (2013.01); *G06T 2207/10081* (2013.01); *G06T 2207/20072* (2013.01); *G06T 2207/20076* (2013.01); *G06T 2207/20081* (2013.01); *G06T 2207/20084* (2013.01); *G06T 2207/20104* (2013.01); *G06T 2207/30096* (2013.01)

(58) Field of Classification Search
CPC ....... A61B 6/5217; A61B 6/54; G06T 7/0012; G06T 2207/10081; G06T 2207/20072; G06T 2207/20076; G06T 2207/20081; G06T 2207/20084; G06T 2207/20104; G06T 2207/30096; G06T 2200/24; G06T 2211/408; G06T 11/008

See application file for complete search history.

(56) References Cited

U.S. PATENT DOCUMENTS

| | | | |
|---|---|---|---|
| 2016/0157802 A1* | 6/2016 | Anderson | A61B 6/032 600/407 |
| 2017/0224299 A1 | 8/2017 | Petschke et al. | |
| 2017/0372193 A1 | 12/2017 | Mailhe et al. | |
| 2019/0374183 A1* | 12/2019 | Li | G16H 50/30 |

OTHER PUBLICATIONS

Extended European Search Report dated Feb. 27, 2020 in European Patent Application No. 19210916.3.
D.P. Clark, et al., "Multi-energy CT decomposition using convolutional neural networks," Proc. of SPIE, vol. 10573, Mar. 2018, 9 pages.

* cited by examiner

TOMOGRAPHIC IMAGE PROCESSING APPARATUS AND METHOD OF SEPARATING MATERIAL OF OBJECT IN SPECTRAL TOMOGRAPHIC IMAGE, AND COMPUTER PROGRAM PRODUCT

CROSS-REFERENCE TO RELATED APPLICATION

This application is based on and claims priority under 35 U.S.C. § 119 to Korean Patent Application No. 10-2018-0146774, filed on Nov. 23, 2018, in the Korean Intellectual Property Office, the disclosure of which is incorporated by reference herein in its entirety.

BACKGROUND

1. Field

The disclosure relates to a tomographic image processing apparatus, a tomographic image processing method, and a computer program product.

2. Description of Related Art

A spectral tomographic image shows attenuation information of radiation that has passed through an object at a plurality of energy levels. The development of spectral tomography has allowed the acquisition of more accurate information about a structure and a status of an object, thereby increasing accuracy of diagnosis by a medical doctor. However, information displayed in an image viewer for displaying a spectral tomographic image is very limited. For example, an image viewer may only display monochromatic images at each energy step or effective-z values for a spectral tomographic image. Thus, the use of spectral tomographic images has a limitation in directly improving diagnostic efficiency.

SUMMARY

Provided are a tomographic image processing apparatus and method, whereby diagnostic efficiency and accuracy may be increased by separating a material of an object in a spectral tomographic image and providing a result of the material separation via a user interface (UI).

Also provided are a tomographic image processing apparatus and method, whereby a diagnosis by a user is facilitated by estimating a predictable tumor or lesion based on a result of material separation in a spectral tomographic image and providing information about the tumor or lesion.

Also provided are a tomographic image processing apparatus and method, whereby accuracy of material separation is improved by training a material separation model via machine learning and using the trained material separation model.

Also provided are a tomographic image processing apparatus and method, whereby the burden of collecting training data is reduced and performance of training is increased by increasing the number of pieces of training data via data augmentation.

Additional aspects will be set forth in part in the description which follows and, in part, will be apparent from the description, or may be learned by practice of the presented embodiments of the disclosure.

According to an embodiment of the disclosure, a tomographic image processing apparatus includes: a display; an input interface configured to receive an external input; a storage storing an input tomographic image of an object; and at least one processor configured to: control the display to display the input tomographic image; determine a material combination to be separated from the input tomographic image; and control the display to display material separation information corresponding to the determined material combination for a region of interest (ROI) selected in the input tomographic image based on the external input, wherein the input tomographic image is a spectral tomographic image comprising a plurality of tomographic images respectively corresponding to a plurality of energy levels.

The at least one processor may be further configured to select the material combination based on a type of the object or the external input.

The storage may further store the material separation information for each pixel in the input tomographic image, and the at least one processor may be further configured to control the display to display the stored material separation information based on the external input for selecting the ROI.

The at least one processor may be further configured to control the display to display information about a tumor or lesion in the input tomographic image of the object.

The at least one processor may be further configured to determine the information about the tumor or lesion based on the material separation information.

The at least one processor may be further configured to obtain a material separation model for acquiring the material separation information based on input tomographic image data of the input tomographic image by using training data which includes a plurality of pieces of spectral tomographic image data and is acquired when information about a proportion of each material and its energy attenuation value are known.

The at least one processor may be further configured to generate augmented training data by fitting a concentration or density to the training data.

The at least one processor may be further configured to: train a deep neural network with the augmented training data; generate a deep neural network model for differentiating the material separation information with respect to each pixel from the input tomographic image data for the input tomographic image; and identify the material separation information in the input tomographic image data by using the deep neural network model.

The input tomographic image data may be raw data of the input tomographic image.

The ROI may be a region including one pixel or a plurality of pixels.

The material separation information may be displayed in a graph form indicating probability information regarding the determined material combination.

The material separation information may be displayed in the input tomographic image as a color map representing a distribution of each material in the determined material combination.

The tomographic image processing apparatus may further include a data acquirer configured to acquire raw data with respect to the object.

According to another embodiment of the disclosure, a tomographic image processing method includes: displaying an input tomographic image of an object; determining a material combination to be separated from the input tomographic image; and displaying material separation information corresponding to the determined material combination for an ROI selected in the input tomographic image based on an external input, wherein the input tomographic image is a spectral tomographic image comprising a plurality of tomographic images respectively corresponding to a plurality of energy levels.

According to another embodiment of the disclosure, a computer program product includes a recording medium having stored therein program commands, when executed by a processor, cause the processor to perform a tomographic image processing method including: displaying an input tomographic image of an object; determining a material combination to be separated from the input tomographic image; and displaying material separation information corresponding to the determined material combination for an ROI selected in the input tomographic image based on an external input, wherein the input tomographic image is a spectral tomographic image comprising a plurality of tomographic images respectively corresponding to a plurality of energy levels.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
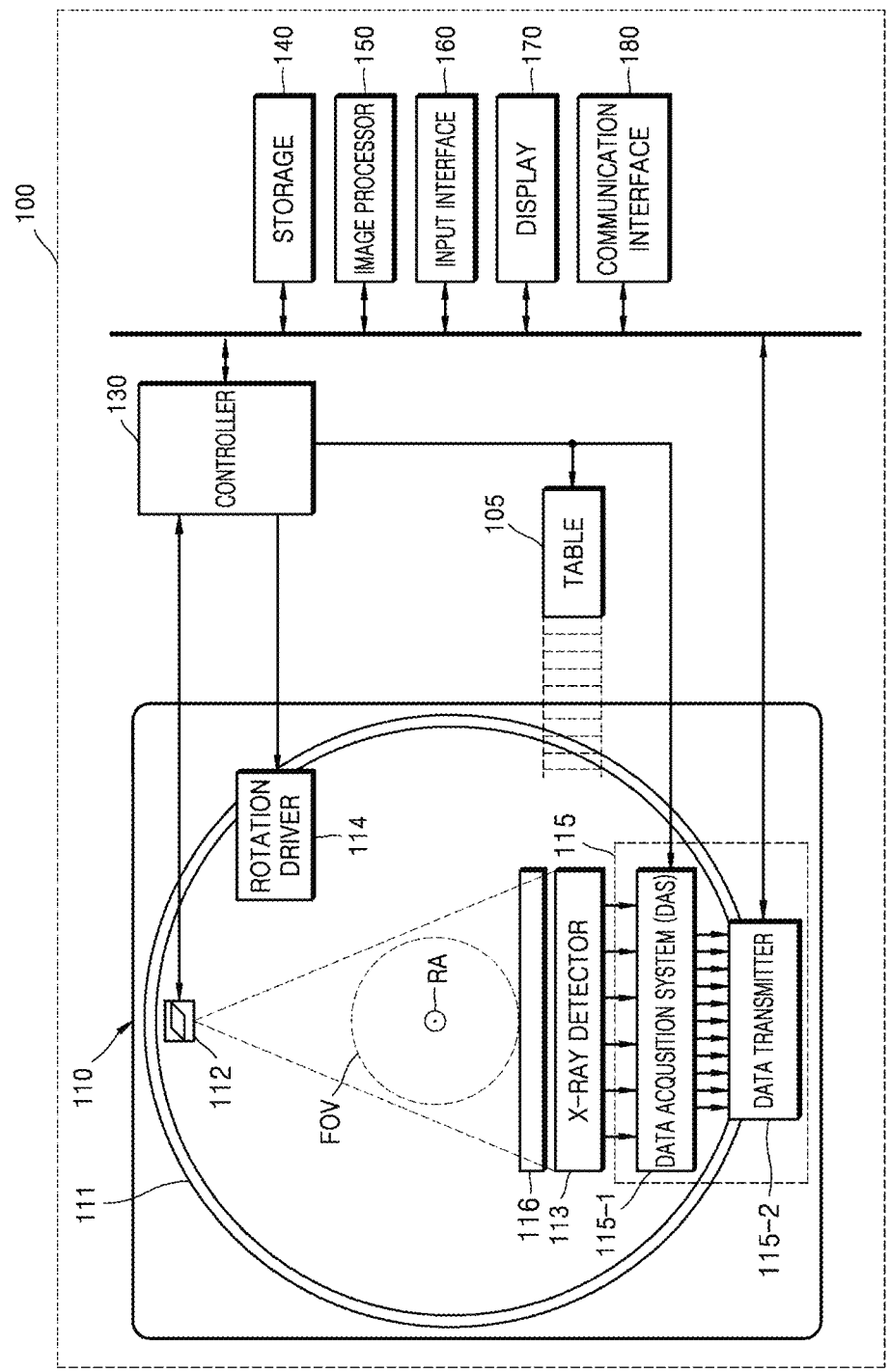
FIG. 1 illustrates a computed tomography (CT) system according to an embodiment of the disclosure.

The principle of the disclosure is explained and embodiments are disclosed so that the scope of the disclosure is clarified and one of ordinary skill in the art to which the disclosure pertains implements the disclosure. The disclosed embodiments may have various forms.

Throughout the disclosure, the expression "at least one of a, b or c" indicates only a, only b, only c, both a and b, both a and c, both b and c, all of a, b, and c, or variations thereof.

Throughout the specification, like reference numerals or characters refer to like elements. In the present specification, all elements of embodiments are not explained, but general matters in the technical field of the disclosure or redundant matters between embodiments will not be described. Terms 'module' or 'unit' used herein may be implemented using at least one or a combination from among software, hardware, or firmware, and, according to embodiments, a plurality of 'module' or 'unit' may be implemented using a single element, or a single 'module' or 'unit' may be implemented using a plurality of units or elements. The operational principle of the disclosure and embodiments thereof will now be described more fully with reference to the accompanying drawings.

In the present specification, an image may include a medical image obtained by a medical imaging apparatus, such as a computed tomography (CT) apparatus, a magnetic resonance imaging (MRI) apparatus, an ultrasound imaging apparatus, or an X-ray apparatus.

Throughout the specification, the term 'object' is a thing to be imaged, and may include a human, an animal, or a part of a human or animal. For example, the object may include a part of a body (i.e., an organ), a phantom, or the like.

In the present specification, a 'CT system' or 'CT apparatus' refers to a system or apparatus configured to emit X-rays while rotating around at least one axis relative to an object and photograph the object by detecting the X-rays.

In the specification, a 'CT image' refers to an image constructed from raw data obtained by photographing an object by detecting X-rays that are emitted as the CT system or apparatus rotates about at least one axis with respect to the object.

FIG. 1 illustrates a structure of a CT system 100 according to an embodiment.

The CT system 100 may include a gantry 110, a table 105, a controller 130, a storage 140, an image processor 150, an input interface 160, a display 170, and a communication interface 180.

The gantry 110 may include a rotating frame 111, an X-ray generator 112, an X-ray detector 113, a rotation driver 114, and a readout device 115.

The rotating frame 111 may receive a driving signal from the rotation driver 114 and rotate around a rotation axis (RA).

An anti-scatter grid 116 may be disposed between an object and the X-ray detector 113 and may transmit most of primary radiation and attenuate scattered radiation. The object may be positioned on the table 105 which may move, tilt, or rotate during a CT scan.

The X-ray generator 112 receives a voltage and a current from a high voltage generator (HVG) to generate and emit X-rays.

The CT system 100 may be implemented as a single-source CT system including one X-ray generator 112 and one X-ray detector 113, or as a dual-source CT system including two X-ray generators 112 and two X-ray detectors 113.

The X-ray detector 113 detects radiation that has passed through the object. For example, the X-ray detector 113 may detect radiation by using a scintillator, a photon counting detector, etc.

Methods of driving the X-ray generator 112 and the X-ray detector 113 may vary depending on scan modes used for scanning of the object. The scan modes are classified into an axial scan mode and a helical scan mode, according to a path along which the X-ray detector 113 moves. Furthermore, the scan modes are classified into a prospective mode and a retrospective mode, according to a time interval during which X-rays are emitted.

The controller 130 may control an operation of each of the components of the CT system 100. The controller 130 may include a memory configured to store program for performing a function or data and a processor configured to process the program codes or the data. The controller 130 may be implemented in various combinations of at least one memory and at least one processor. The processor may generate or delete a program module according to an operating status of the CT system 100 and process operations of the program module.

The readout device 115 receives a detection signal generated by the X-ray detector 113 and outputs the detection signal to the image processor 150. The readout device 115 may include a data acquisition system (DAS) 115-1 and a data transmitter 115-2. The DAS 115-1 uses at least one amplifying circuit to amplify a signal output from the X-ray detector 113, and outputs the amplified signal. The data transmitter 115-2 uses a circuit such as a multiplexer (MUX) to output the signal amplified in the DAS 115-1 to the image processor 150. According to a slice thickness or a number of slices, only some of a plurality of pieces of data collected by the X-ray detector 113 may be provided to the image processor 150, or the image processor 150 may select only some of the plurality of pieces of data.

The image processor 150 obtains tomography data from a signal obtained by the readout device 115 (e.g., pure data that is data before being processed). The image processor 150 may pre-process the obtained signal, convert the obtained signal into tomography data, and post-process the tomography data. The image processor 150 may perform some or all of the processes described herein, and the type or order of processes performed by the image processor 150 may vary according to embodiments.

The image processor 150 may perform pre-processing, such as a process of correcting sensitivity irregularity between channels, a process of correcting a rapid decrease of signal strength, or a process of correcting signal loss due to an X-ray absorbing material, on the signal obtained by the readout device 115.

According to embodiments, the image processor 150 may perform some or all of the processes for reconstructing a tomographic image, to thereby generate the tomography data. According to an embodiment, the tomography data may be in the form of data that has undergone back-projection, or in the form of a tomographic image. According to embodiments, additional processing may be performed on the tomography data by an external device such as a server, a medical apparatus, or a portable device.

Raw data is a set of data values corresponding to intensities of X-rays that have passed through the object, and may include projection data or a sinogram. The data that has undergone back-projection is obtained by performing back-projection on the raw data by using information about an angle at which X-rays are emitted. The tomographic image is obtained by using image reconstruction techniques including back-projection of the raw data.

The storage 140 is a storage medium for storing control-related data, image data, etc., and may include a volatile or non-volatile storage medium.

The input interface 160 receives control signals, data, etc., from a user. The display 170 may display information indicating an operational status of the CT system 100, medical information, medical image data, etc.

The CT system 100 includes the communication interface 180 and may be connected to external devices, such as a server, a medical apparatus, and a portable device (smartphone, tablet personal computer (PC), wearable device, etc.), via the communication interface 180.

The communication interface 180 may include one or more components that enable communication with an external device. For example, the communication interface 180 may include a short distance communication module, a wired communication module, and a wireless communication module.

According to embodiments, the CT system 100 may or may not use contrast media during a CT scan, and may be implemented as a device connected to other equipment.

Figure 2:
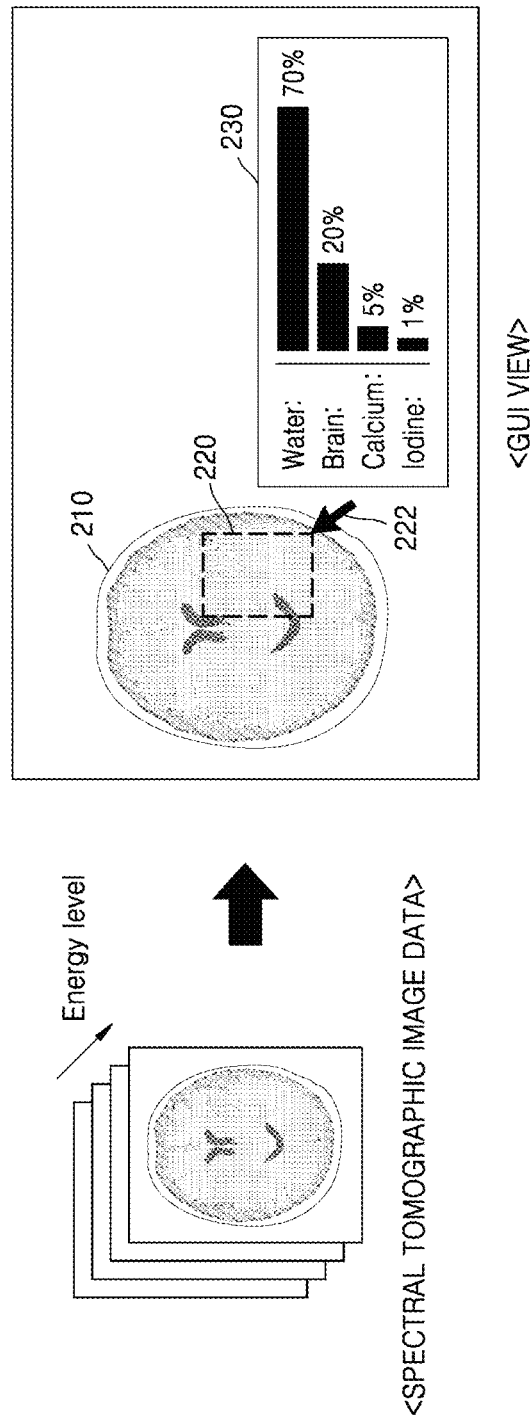
FIG. 2 illustrates a process of providing material separation information from an input tomographic image, according to an embodiment of the disclosure.

FIG. 2 illustrates a process of providing material separation information from an input tomographic image, according to an embodiment of the disclosure.

A spectral tomographic image is an image representing information about attenuation of radiation at a plurality of energy levels. Spectral tomographic image data may be acquired by scanning an object at a plurality of energy levels or by using a photon counting detector (PCD). For example, a CT system 100 may perform spectral tomography imaging according to dual-energy CT imaging utilizing a plurality of tubes in the X-ray generator 112 for a plurality of energy levels, a method of switching a tube voltage, a method of adjusting an energy level of a tube, a method using a plurality of X-ray detectors for detecting radiation having different energy levels, a method using an X-ray detector made of a plurality of layers respectively corresponding to different energy levels, etc. The spectral tomographic image data may be acquired via a PCD including an integrated circuit for each pixel, which quantizes an energy level of a photon. Spectral tomographic image data refers to raw data acquired via the X-ray detector 113. A spectral tomographic image refers to a tomographic image reconstructed from raw data. A tomographic image may be represented by gray levels based on a Hounsfield unit (HU) value. Spectral tomography imaging is an operation of scanning an object in order to acquire spectral tomographic image data.

Materials in the object demonstrate different attenuation profiles when X-rays emitted by the X-ray generator 112 pass through the materials. The attenuation profiles may vary depending on the type and density/concentration of a material. A spectral tomographic image includes information about attenuation profiles that are different for each energy level. According to embodiments of the disclosure, material separation information 230 acquired based on a tomographic image 210 that is a spectral tomographic image is provided to a user via a graphical user interface (GUI).

According to embodiments of the disclosure, the material separation information 230 is provided with respect to a position or region selected by the user in the tomographic image 210. The GUI may provide the material separation information 230 corresponding to an ROI 220 including a point or a region selected by the user in the tomographic image 210. The material separation information 230 may include the type of a material corresponding to the ROI 220 and probability information indicating a probability that the ROI 220 corresponds to a specific material. The ROI 220 may be selected by the user via a cursor 222, a touch input, etc.

Figure 3:
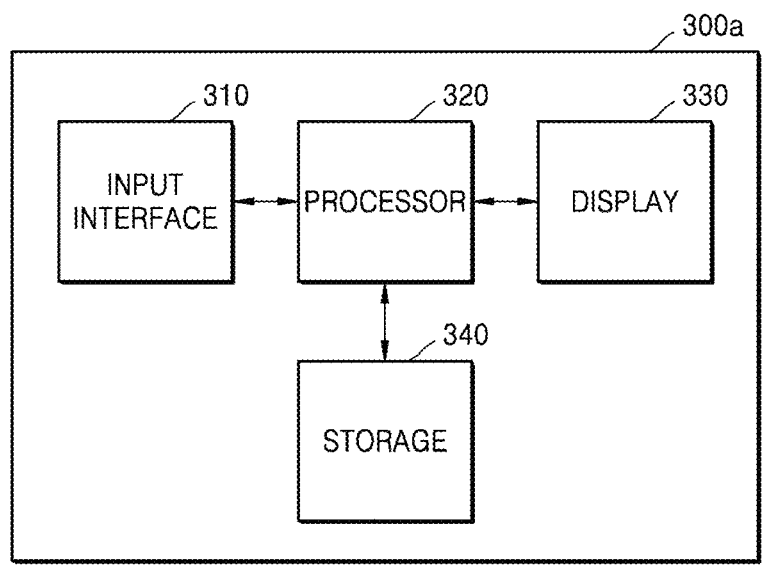
FIG. 3 is a block diagram of a structure of a tomographic image processing apparatus according to an embodiment of the disclosure.

FIG. 3 is a block diagram of a structure of a tomographic image processing apparatus 300*a* according to an embodiment of the disclosure.

The tomographic image processing apparatus 300*a* may be implemented in the form of a CT system, a general-purpose computer, a portable terminal, or a kiosk. For example, the portable terminal may be implemented as a smartphone, a tablet personal computer (PC), etc. For example, the CT system may be implemented as the CT system 100 of FIG. 1.

According to an embodiment of the disclosure, the tomographic image processing apparatus 300*a* includes an input interface 310, a processor 320, a display 330, and a storage 340.

The input interface 310 receives an external input. The input interface 310 may receive a user input or an input from an external device. According to an embodiment of the disclosure, the input interface 310 may be implemented as a manipulator for receiving a user input. For example, the input interface 310 may include a mouse, a trackball, a keyboard, a key, a button, a touch pad, a touch screen, a jog switch, etc. As another example, the input interface 310 may be implemented as an input/output (I/O) device or transceiver for receiving a control signal input from an external device.

The processor 320 may control all operations of the tomographic image processing apparatus 300*a* and process data. The processor 320 may include at least one processor.

According to an embodiment of the disclosure, the processor 320 performs all operations of controlling the gantry (110 of FIG. 1) and processing raw data and may be implemented as one or a plurality of processors. According to another embodiment of the disclosure, the processor 320 may correspond to one or more processors for processing raw data received from an external device. The processor 320 may correspond to the image processor 150 of FIG. 1 or a combination of the image processor 150 and the controller 130 of FIG. 1.

The processor 320 displays an input tomographic image of an object on the display 330. The processor 320 controls the display 330 to display the input tomographic image of the object. When an input tomographic image is received, the processor 320 may display the input tomographic image via a GUI of the tomographic image processing apparatus 300*a*. In this case, the input tomographic image may include a single energy tomographic image and a spectral tomographic image. According to an embodiment of the disclosure, the signal energy tomographic image and the spectral tomographic image may be sequentially input as the input tomographic image, or only the spectral tomographic image may be input as such.

The processor 320 may determine a material combination to be separated from the input tomographic image. The material combination is a combination of materials to be separated from the input tomographic image. For example, the material combination may be determined as a water/brain or water/brain/calcium combination. The object may include a plurality of materials, and various material combinations may be derived from the plurality of materials. In this case, a material separation model may vary according to a material combination for separating materials. After determining the material combination, the processor 320 determines a material separation model to be used. The processor 320 may determine a material combination automatically or according to an external input such as a user input.

The processor 320 displays, on the display 330, material separation information corresponding to the determined material combination for an ROI selected in an input tomographic image based on an external input. The processor 320 determines an ROI based on an external input received via the input interface 310 The ROI may correspond to a region including at least one pixel. When the ROI is determined, the processor 320 performs material separation on the ROI by using the determined material separation model and acquires material separation information In this case, the material separation information is information indicating a probability that each pixel or unit region corresponds to each material, or the type of a material corresponding to each pixel or unit region. The processor 320 displays the material separation information with respect to the ROI on the display 330.

The display 330 displays a GUI view of the tomographic image processing apparatus 300*a*. The display 330 may correspond to the display 170 of FIG. 1.

The storage 340 stores an input tomographic image. The storage 340 stores store various data or instructions necessary for an operation of the tomographic image processing apparatus 300*a*. According to an embodiment of the disclosure, the storage 340 may store a pre-generated material separation model and material separation information generated by applying the material separation model to an input tomographic image.

The storage 340 may be formed as a volatile or nonvolatile memory. According to an embodiment of the disclosure, the storage 340 may correspond to the storage 140 of FIG. 1.

Figure 4:
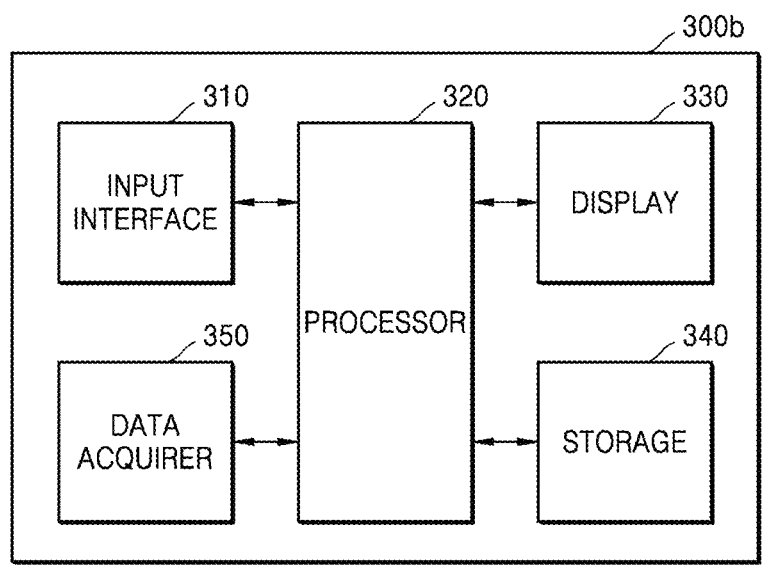
FIG. 4 is a block diagram of a structure of a tomographic image processing apparatus according to another embodiment of the disclosure.

FIG. 4 is a block diagram of a structure of a tomographic image processing apparatus 300b according to another embodiment of the disclosure.

According to another embodiment of the disclosure, the tomographic image processing apparatus 300b may further include the data acquirer 350 in comparison to the tomographic image processing apparatus 300a described with reference to FIG. 3.

The data acquirer 350 acquires raw data by scanning an object. The raw data may correspond to projection data or a sinogram. The raw data may correspond to raw data acquired by performing spectral tomography imaging.

According to an embodiment of the disclosure, the data acquirer 350 may correspond to a scanner for acquiring raw data by scanning an object via X-rays. For example, the scanner may include the X-ray generator 112 and the X-ray detector 113 described with reference to FIG. 1. According to the embodiment of the disclosure, the data acquirer 350 may acquire raw data by scanning an object according to a protocol set under control by the processor 320.

According to another embodiment of the disclosure, the data acquirer 350 may to a communication interface or I/O device via which raw data is acquired from an external device. Examples of the external device include a CT system, a medical data server, another user's terminal, etc. According to the embodiment of the disclosure, the data acquirer 350 may be connected to an external device via various wired or wireless networks such as a wired cable, a local area network (LAN), a mobile communication network, the Internet, etc. The data acquirer 350 may correspond to the communication interface 180 of FIG. 1.

Figure 5:
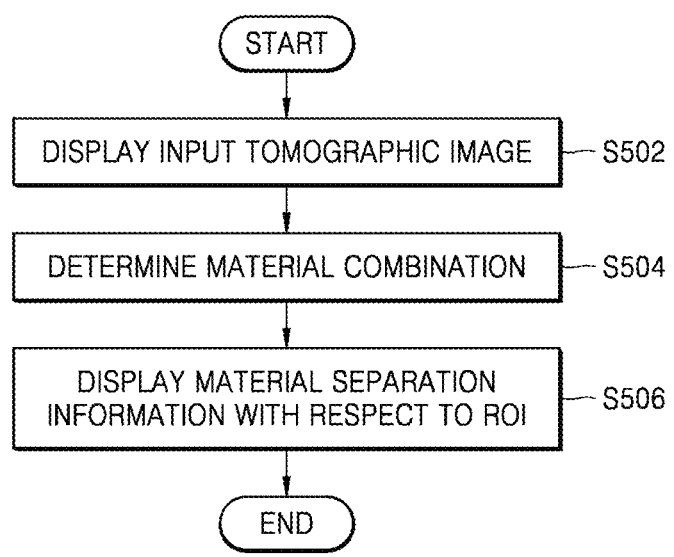
FIG. 5 is a flowchart of a tomographic image processing method, according to an embodiment of the disclosure.

FIG. 5 is a flowchart of a tomographic image processing method according to an embodiment of the disclosure.

According to embodiments of the disclosure, operations of the tomographic image processing method may be performed by various types of electronic devices including a processor, a display, an input interface, and a storage. The present specification focuses on an embodiment of the disclosure in which the tomographic image processing apparatuses 300a or 300b according to the disclosure performs a tomographic image processing method, according to the disclosure. Thus, embodiments of the disclosure described with respect to the tomographic image processing apparatuses 300a and 300b may be applied to a tomographic image processing method, and embodiments of the disclosure described with respect to a tomographic image processing method may be applied to the embodiments of the disclosure described with respect to the tomographic image processing apparatuses 300a and 300b. Although it has been described that tomographic image processing methods according to embodiments of the disclosure are performed by the tomographic image processing apparatus 300a or 300b according to the disclosure, embodiments of the disclosure are not limited thereto, and the tomographic image processing methods may be performed by various types of electronic devices.

A tomographic image processing apparatus displays an input tomographic image on a display (S502).

Next, the tomographic image processing apparatus determines a material combination to be subjected to material separation in the input tomographic image (S504). When the material combination is determined, the tomographic image processing apparatus may then determine a material separation model corresponding to the material combination and acquire material separation information based on the input tomographic image.

Then, the tomographic image processing apparatus displays the material separation information with respect to an ROI in the input tomographic image selected according to an external input (S506).

Figure 6:
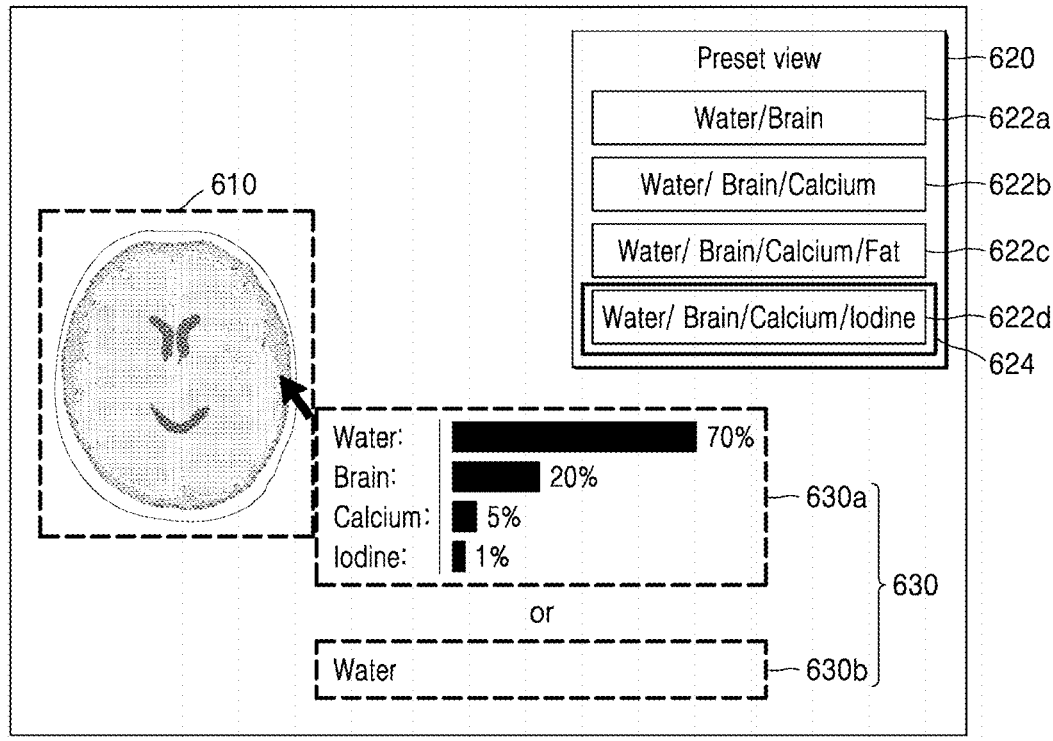
FIG. 6 illustrates a graphical user interface (GUI) view according to an embodiment of the disclosure.

FIG. 6 illustrates a GUI view according to an embodiment of the disclosure.

According to an embodiment of the disclosure, the GUI view may include an input tomographic image 610, a material combination selection region 620, and material separation information 630.

The material combination selection region 620 shows material combination options 622a through 622d selectable by the user, and provides a UI that allows the user to select one of the material combination options 622a through 622d. For example, the user may select a desired material combination by moving a selection box 624.

The material separation information 630 includes probability information indicating a probability that the ROI selected by the user corresponds to each material in the selected material combination. According to an embodiment of the disclosure, material separation information 630a may represent in a graph the probability that the ROI corresponds to each material. The graph may be provided together with information indicating a numerical value corresponding to each material. According to another embodiment of the disclosure, material separation information 630b may include information about the type of a material corresponding to the ROI. For example, when the probability that the ROI corresponds to a specific material is greater than or equal to a reference value (e.g., 99%), the material separation information 630b may include information about the type of the material corresponding to the ROI without its probability information.

Figure 7:
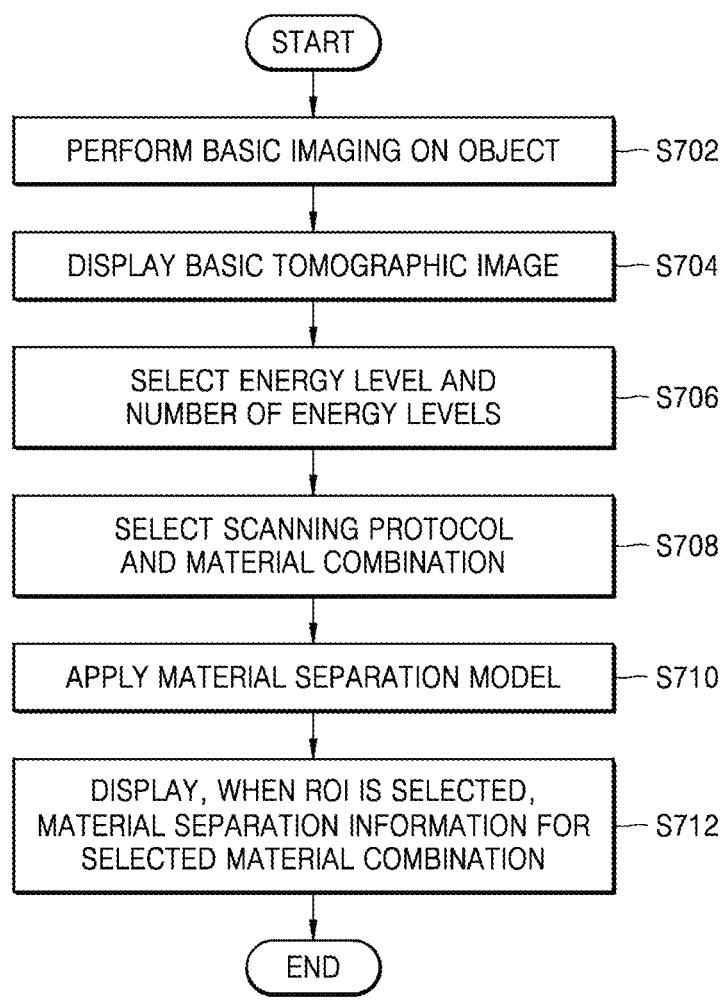
FIG. 7 is a flowchart of a tomographic image processing method, according to an embodiment of the disclosure.

FIG. 7 is a flowchart of a method of a tomographic image processing method according to an embodiment of the disclosure.

According to an embodiment of the disclosure, a tomographic image processing apparatus performs both an operation of scanning the object and material separation operation. The tomographic image processing apparatus may control spectral CT imaging at a plurality of energy levels by controlling a scanning unit provided therein or by controlling a CT system connected thereto, and acquire a spectral tomographic image.

First, the tomographic image processing apparatus performs basic imaging on the object (S702). In this case, the basic imaging may be single energy imaging performed at a predetermined energy level. The basic imaging may be performed according to a protocol that is set by the user or automatically set.

Next, the tomographic image processing apparatus displays a basic tomographic image obtained by performing the basic imaging (S704).

Then, at least one energy level at which spectral tomography imaging is to be performed and the number of energy levels are selected (S706). The energy level and the number of energy levels may be selected according to a user input. The tomographic image processing apparatus may provide a GUI for selecting an energy level and the number of energy levels and receive a user input of selecting the energy level and the number of energy levels. Furthermore, the tomographic image processing apparatus may provide, via the GUI, information about selectable energy levels and the selectable number of energy levels.

Furthermore, the tomographic image processing apparatus selects a scanning protocol and a material combination (S708). Operations S706 and S708 may be performed in a different order than described above or be performed simultaneously. The tomographic image processing apparatus may select the scanning protocol and the material combination based on a user input. The tomographic image processing apparatus may provide a GUI for selecting the scanning protocol and the material combination. The scanning protocol may be the same as or different from a protocol for performing the basic imaging in operation S702.

According to an embodiment of the disclosure, when the user selects a scanning protocol, the tomographic image processing apparatus may provide information about material combinations that are selectable for the selected scanning protocol. The user may select one of the selectable material combinations.

According to another embodiment of the disclosure, when the user selects a material combination, the tomographic image processing apparatus automatically recommend or select scanning protocols to be performed in order to perform material separation on the selected material combination. The user may select one of the scanning protocols recommended by the tomographic image processing apparatus.

According to an embodiment of the disclosure, when an energy level, the number of energy levels, and a scanning protocol are determined, the tomographic image processing apparatus may perform spectral tomography imaging based thereon, and a material combination may be selected before or after performing the spectral tomography imaging. The selected material combination may be changed even after performing the spectral tomography imaging.

According to another embodiment of the disclosure, when a material combination is selected, the tomographic image processing apparatus may automatically recommend energy levels, the number of energy levels, and scanning protocols for performing material separation on the selected material combination, and the user may select an energy level, the number of energy levels, and a scanning protocol based on the recommendation information. Because the greater the number of materials in the material combination, the greater the number of energy levels required, the tomographic image processing apparatus may select the number of energy levels based on the number of materials. Furthermore, the tomographic image processing apparatus may determine and recommend, based on the type of materials in the material combination, a combination of energy levels at which a difference in attenuation profile is large for each material. Furthermore, the tomographic image processing apparatus may select and recommend a scanning protocol to be performed in order to perform material separation on the material combination selected by the user.

After the spectral tomography imaging is completed and the material combination is selected, the tomographic image processing apparatus applies to spectral tomographic image data a material separation model corresponding to the selected material combination (S710). By applying the material separation model to the spectral tomographic image data, the tomographic image processing apparatus acquires material separation information for each pixel for storage. The material separation model may be prestored in the tomographic image processing apparatus. The material separation model may be determined based on a material combination and energy levels at which a scan is performed.

The tomographic image processing apparatus may display a basic tomographic image or spectral tomographic image on a display and receive a selection of an ROI via the GUI. The user may select the ROI in a tomographic image displayed on the display. The ROI may be a predetermined region including one or a plurality of pixels. When the user selects the ROI, the tomographic image processing apparatus may generate or calculate material separation information for the selected ROI, which indicates a probability that the ROI corresponds to each material in the material combination, and display the generated material separation information (S712). The tomographic image processing apparatus may generate material separation information with respect to the selected ROI based on material separation information previously generated by applying a material separation model.

Figure 8:
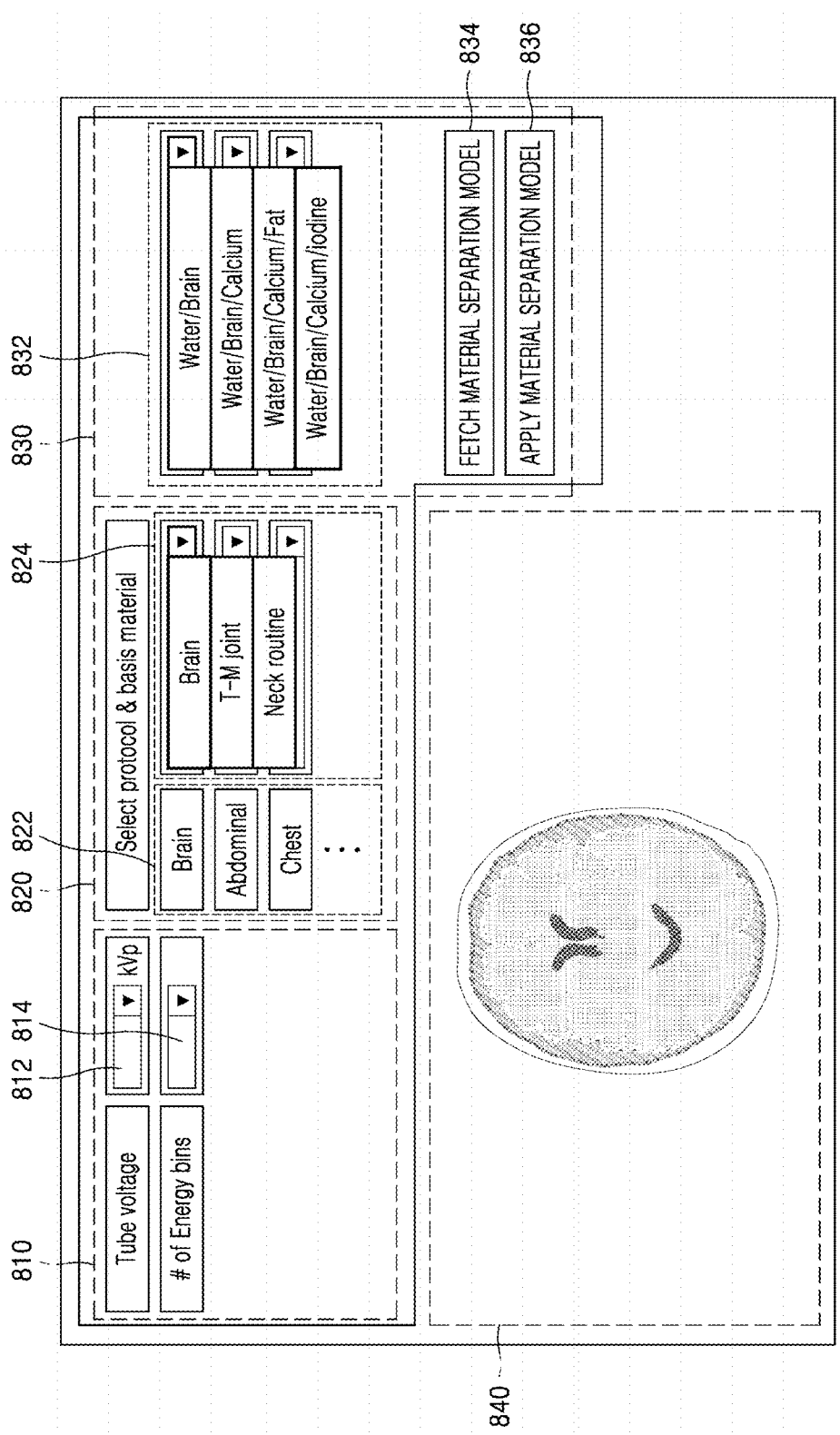
FIG. 8 illustrates a GUI view displayed by a tomographic image processing apparatus, according to an embodiment of the disclosure.

FIG. 8 illustrates a GUI view displayed by a tomographic image processing apparatus, according to an embodiment of the disclosure.

According to an embodiment of the disclosure, the GUI view includes first through fourth regions 810, 820, 830, and 840. The arrangement, size, and combination of the first through fourth regions 810, 820, 830, and 840 may vary according to an embodiment of the disclosure, and the first through fourth regions 810, 820, 830, and 840 may be merged with or overlapped by one another. According to an embodiment of the disclosure, at least one of the first, second, third, or fourth region 810, 820, 830, or 840, or a combination thereof may be displayed in another view or menu by an external device.

The first region 810 is a region for setting values of parameters necessary to perform spectral tomography imaging. The first region 810 may include a 1-1 UI element 812 for setting an energy level and a 1-2 UI element 814 for setting the number of energy levels. The type and values of the parameters in the first region 810 may vary depending on a configuration of a scanning unit for performing spectral tomography imaging or a spectral tomography imaging mode.

The second region 820 is a region for selecting a scanning protocol and the type of an object. The second region 820 includes a 2-1 UI element 822 for selecting the type of the object and a 2-2 UI element 824 for selecting a scanning protocol. When the type of the object is selected in the 2-1 UI element 822, the tomographic image processing apparatus may provide via the 2-2 UI element 824 information about at least one scanning protocol that is to be performed on the selected object. For example, when the brain is selected in the 2-1 UI element 822, in the 2-2 UI element 824 may provide Brain, T-M joint, and Neck routine, which are scanning protocols to be performed on the brain, as information about selectable scanning protocols. The user may select a scanning protocol by selecting one of the selectable scanning protocols in the 2-2 UI element 824.

The third region 830 is a region for selecting a material combination. The third region 830 may include a 3-1 UI element 832 for selecting a material combination. The 3-1 UI element 832 may provide information about at least one material combination selectable for the object selected by the user. For example, when the user selects the brain in the 2-1 UI element 822, the 3-1 UI element 832 may provide as options Water/Brain, Water/Brain/Calcium, Water/Brain/Calcium/Fat, and Water/Brain/Calcium/Iodine combinations material combinations that are selectable material combinations for the brain. The user may select a material combination by selecting one of the at least one option in the 3-1 UI element 832.

According to another embodiment of the disclosure, the third region 830 may further include a 3-2 UI element 834 for fetching a material separation model corresponding to the selected material combination and a 3-3 UI element 836 for applying the selected material separation model to a spectral tomographic image.

After selecting the material combination, the user may fetch a corresponding material separation model via the 3-2 UI element 834. The tomographic image processing apparatus may generate therein or retrieve therefrom a material separation model corresponding to the selected material combination, or acquire the material separation model from an external device or server.

The user may apply via the 3-3 UI element 836 the material separation model to acquired spectral tomographic image data. When the material separation model is selected via the 3-3 UI element 836, material separation information for each pixel is acquired based on the spectral tomographic image data.

The fourth region 840 is a region where a tomographic image is displayed. A tomographic image obtained via basic or spectral tomography imaging may be displayed in the fourth region 840. Furthermore, material separation information may be displayed in the fourth region 840, together with the tomographic image.

Figure 9:
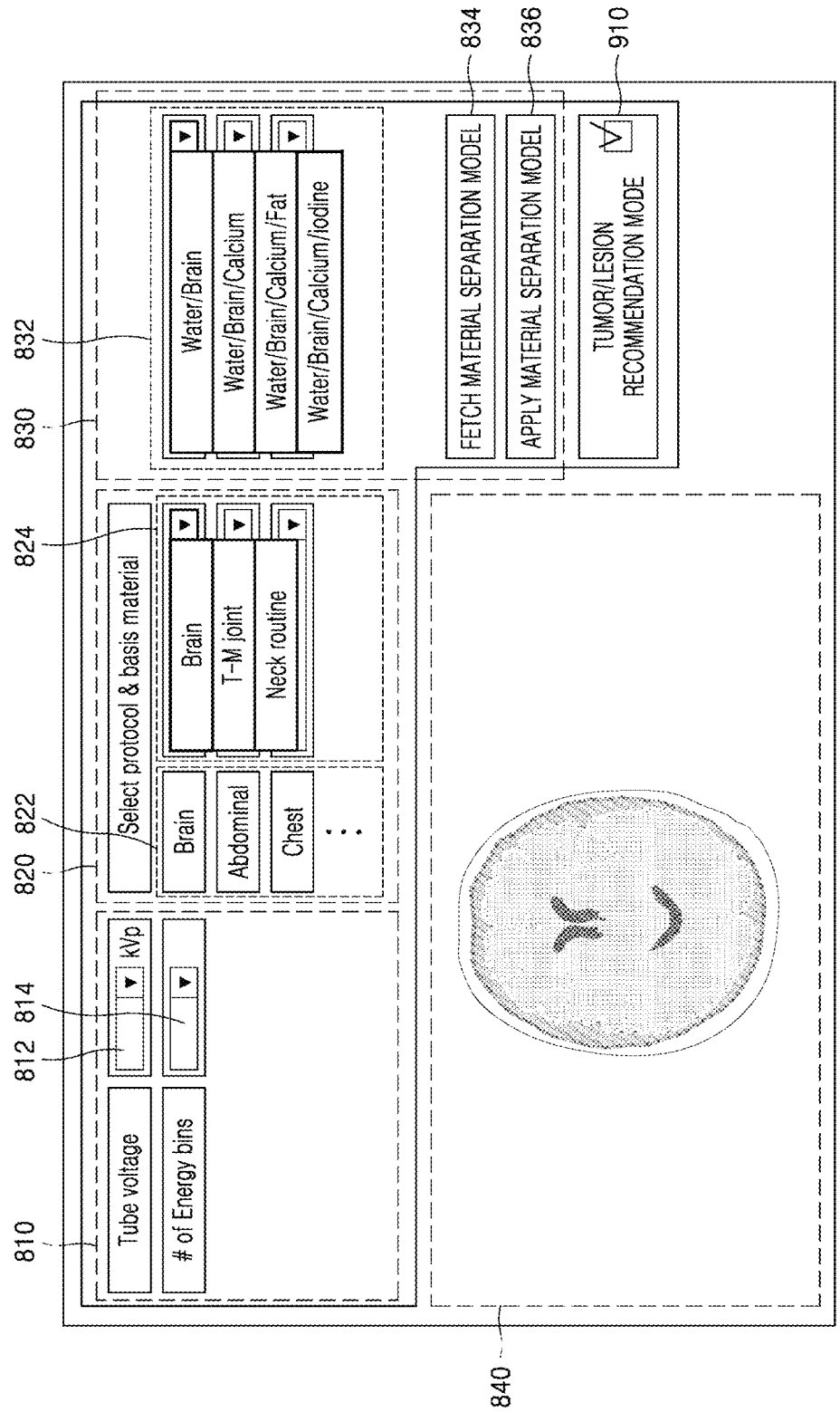
FIG. 9 illustrates a GUI view displayed by a tomographic image processing apparatus, according to an embodiment of the disclosure.

FIG. 9 illustrates a GUI view displayed by a tomographic image processing apparatus, according to an embodiment of the disclosure.

According to an embodiment of the disclosure, the tomographic image processing apparatus may provide a tumor/lesion recommendation mode. In the tumor/lesion recommendation mode, the tomographic image processing apparatus may detect a region suspected to be a tumor/lesion based on material separation information. To achieve this, the GUI view for the tomographic image processing apparatus may further include a fifth UI element 910 for selecting or cancelling the tumor/lesion recommendation mode.

Figure 10:
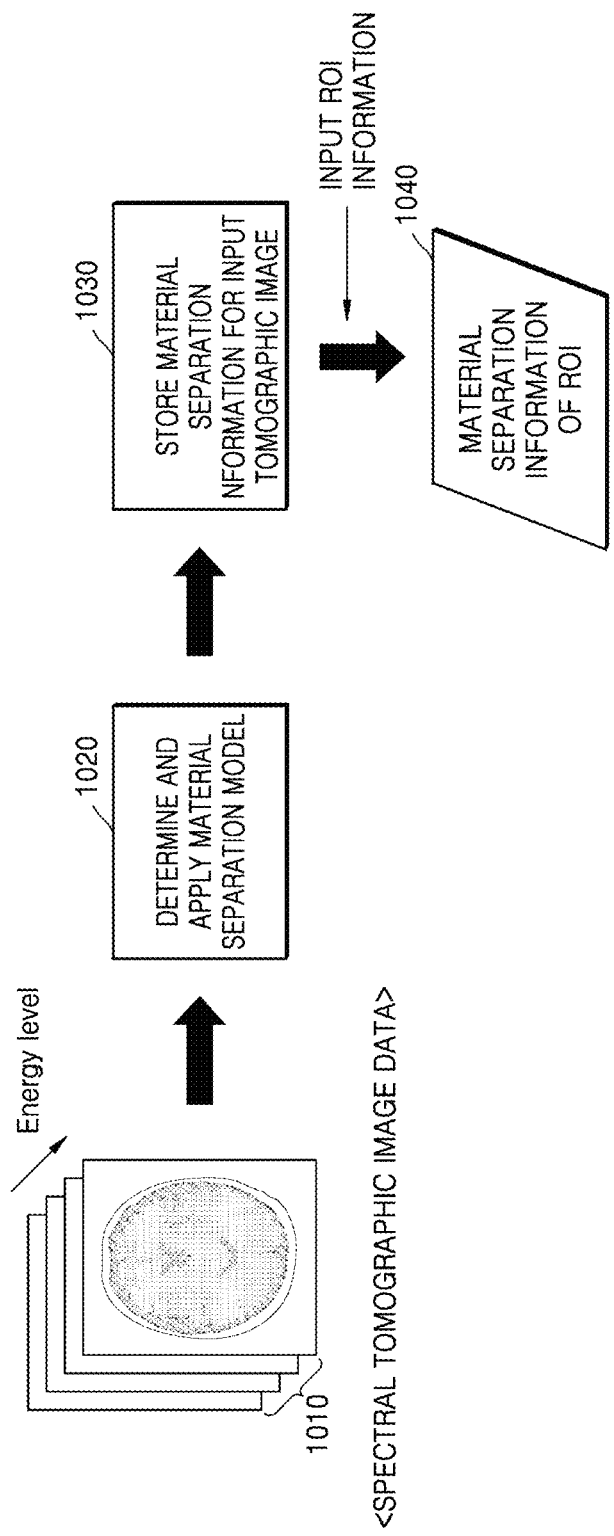
FIG. 10 illustrates a process of acquiring material separation information, according to an embodiment of the disclosure.

FIG. 10 illustrates a process of acquiring material separation information, according to an embodiment of the disclosure.

A tomographic image processing apparatus acquires material separation information by using spectral tomographic image data 1010. The spectral tomographic image data 1010 means raw data acquired by performing spectral tomography imaging. The spectral tomographic image data 1010 represents attenuation information of radiation at a plurality of energy levels or in a plurality of energy ranges.

The tomographic image processing apparatus determines a material separation model and applies the same to the spectral tomographic image data 1010 (1020). As described above, the material separation model may be determined according to a material combination.

The tomographic image processing apparatus stores, in a storage, material separation information for each pixel, which is generated by applying the material separation model to the spectral tomographic image data 1010 (1030). By pregenerating material separation information for all pixels in a tomographic image and storing the same, it is possible to provide in near real-time material separation information with respect to an ROI selected by the user.

Next, when information about the ROI is input, the tomographic image processing apparatus generates and outputs material separation information with respect to the ROI (1040). The tomographic image processing apparatus may display the material separation information near the ROI selected by the user.

Figure 11:
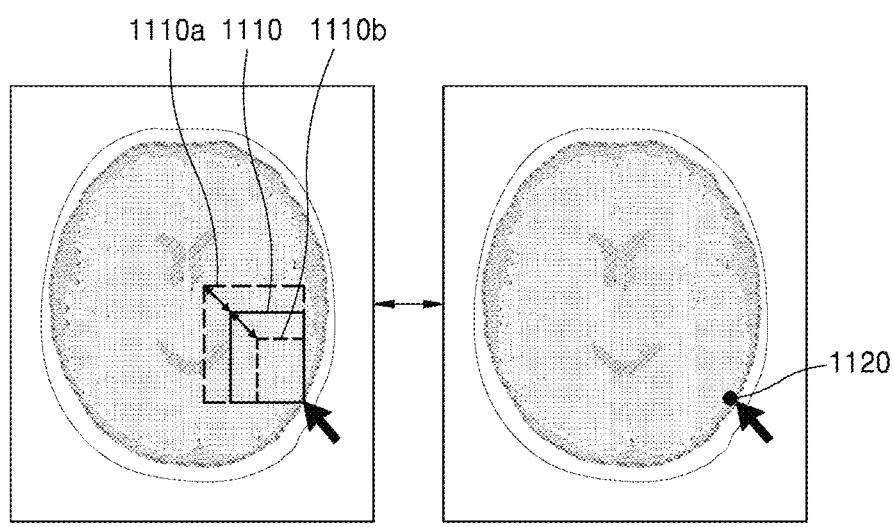
FIG. 11 illustrates a process of selecting a region of interest (ROI), according to an embodiment of the disclosure.

FIG. 11 illustrates a process of selecting an ROI according to an embodiment of the disclosure.

According to an embodiment of the disclosure, the tomographic image processing apparatus may provide a GUI that allows a user to select an ROI in a displayed tomographic image. The tomographic image processing apparatus may receive an external input for selecting an ROI via an input interface.

According to an embodiment of the disclosure, the ROI may be defined as a region 1110 including a plurality of pixels. The user may select a predetermined region via a cursor or a touch input. Furthermore, the user may change a size of the selected ROI (1110a and 1110b). According to the embodiment of the disclosure, the tomographic image processing apparatus may generate material separation information with respect to the selected ROI by extracting pieces of material separation information corresponding to pixels in the selected ROI from among pieces of material separation information corresponding to all pixels, which are generated by applying the material separation model, and merging together the extracted pieces of material separation information.

According to another embodiment of the disclosure, the ROI may correspond to a single pixel 1120. The user may set the pixel 1120 as the ROI by clicking or touching a predetermined point via the input interface. The tomographic image processing apparatus may extract material separation information corresponding to the selected pixel 1120 from the pieces of material separation information corresponding to all the pixels and provide the extracted material separation information via a display.

Figure 12:
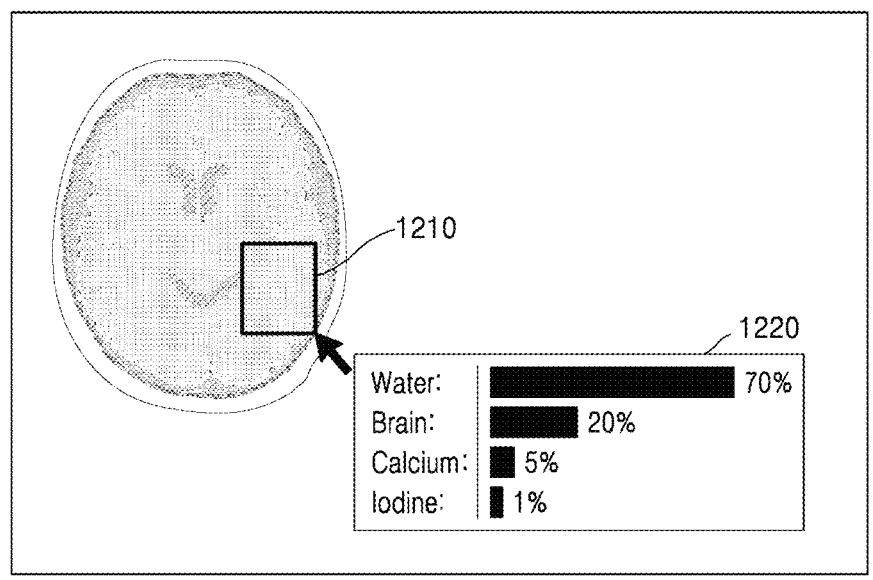
FIG. 12 illustrates a GUI view for providing material separation information with respect to an ROI, according to an embodiment of the disclosure.

FIG. 12 illustrates a GUI view for providing material separation information 1220 with respect to an ROI 1210, according to an embodiment of the disclosure.

According to an embodiment of the disclosure, the material separation information 1220 with respect to the ROI 1210 may indicate the probability that the ROI 1210 corresponds to each material in a selected material combination. For example, as shown in FIG. 12, probabilities that the ROI 1210 correspond to water, brain, calcium, and iodine may be 70%, 20%, 5%, and 1%, respectively.

Figure 13:
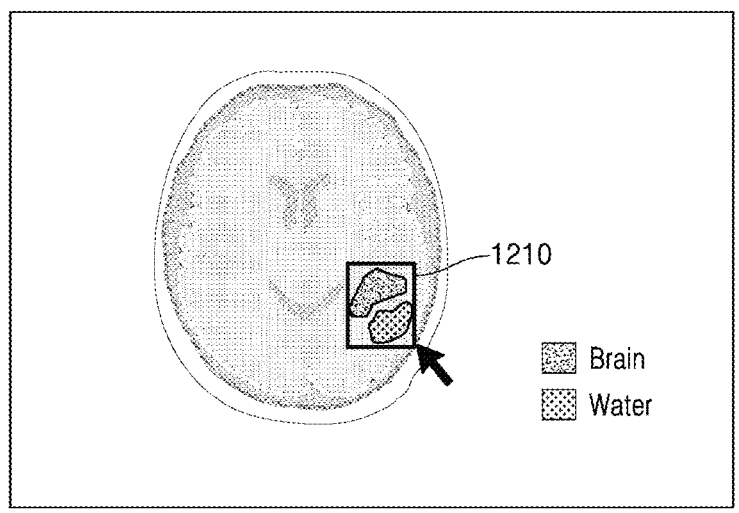
FIG. 13 illustrates a GUI view for providing material separation information with respect to an ROI, according to an embodiment of the disclosure.

FIG. 13 illustrates a GUI view for providing material separation information with respect to the ROI 1210, according to an embodiment of the disclosure.

According to an embodiment of the disclosure, material separation information with respect to the ROI 1210 may be represented as a color map. The color map may indicate the type of a material having a highest probability value. According to an embodiment of the disclosure, when a certain pixel or region includes a first material having a probability value greater than or equal to a reference value, the tomographic image processing apparatus may display the pixel or region in a color corresponding to the first material. Otherwise, when the pixel or region does not include a material having a probability value greater than or equal to the reference value, the tomographic image processing apparatus may not display the pixel or region in any color. According to an embodiment of the disclosure, only materials in a material combination selected by the user may be displayed as a color map while a material not selected by the user is not displayed in any color.

Referring to FIG. 13, the tomographic image processing apparatus may display regions corresponding to the brain and water in the ROI 1210 as a color map.

Figure 14:
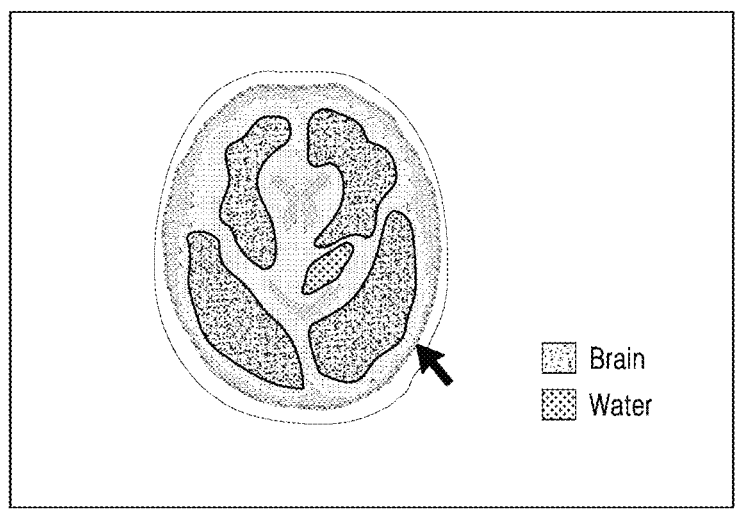
FIG. 14 illustrates a GUI view for providing material separation information with respect to an ROI, according to an embodiment of the disclosure.

FIG. 14 illustrates a GUI view for providing material separation information with respect to an ROI, according to an embodiment of the disclosure.

According to an embodiment of the disclosure, a color map may be displayed across the entire region of an object in a tomographic image. According to an embodiment of the disclosure, only materials in a material combination selected by the user may be displayed as a color map while a material not selected by the user is not displayed in any color.

Figure 15:
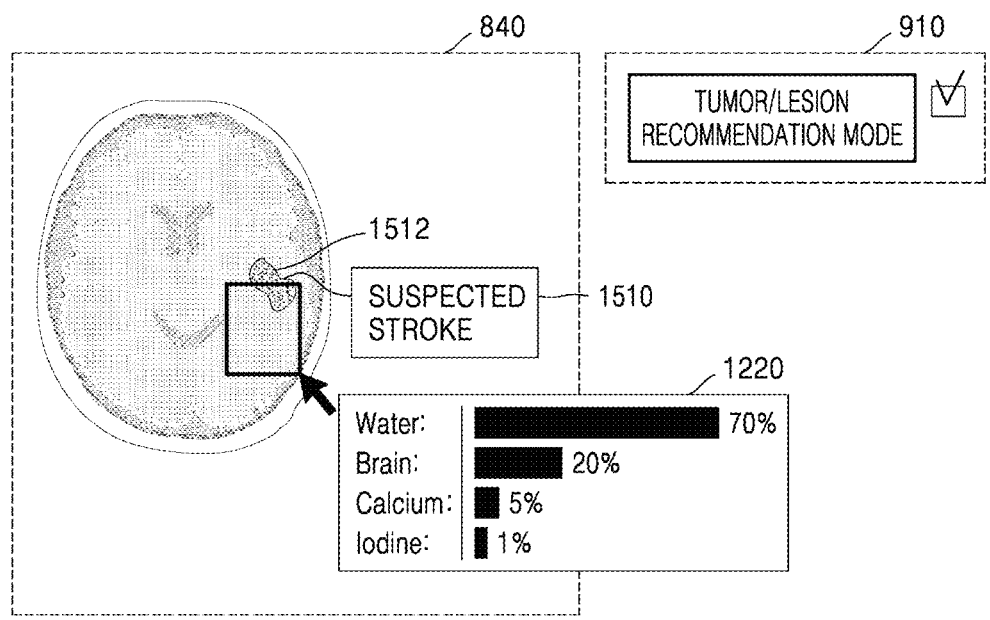
FIG. 15 illustrates a GUI view for providing information about a tumor or lesion in a tumor/lesion recommendation mode, according to an embodiment of the disclosure.

FIG. 15 illustrates a GUI view for providing information about a tumor or lesion in a tumor/lesion recommendation mode, according to an embodiment of the disclosure.

According to an embodiment of the disclosure, when a tumor/lesion recommendation mode is selected, the tomographic image processing apparatus may provide information about a tumor or lesion. The tomographic image processing apparatus may acquire information about a tumor or lesion based on material separation information. For example, the tomographic image processing apparatus may determine that a region having a high probability of being a material corresponding to a tumor corresponds to the tumor and provide information indicating that the region corresponds to the tumor. For this purpose, the tomographic image processing apparatus may prestore disease information indicating information about a material corresponding to at least one tumor or lesion or acquire the disease information from an external device, and generate information about the tumor or lesion based on the disease information.

According to an embodiment of the disclosure, information about a tumor or lesion may be provided only for an ROI. According to another embodiment of the disclosure, information about a tumor or lesion may be provided for the entire region of an object. For example, as shown in FIG. 15, the tomographic image processing apparatus may identify a suspicious region 1512 where a stroke is suspected of having occurred in the object and provide disease information 1510 regarding the suspicious region 1512.

Figure 16:
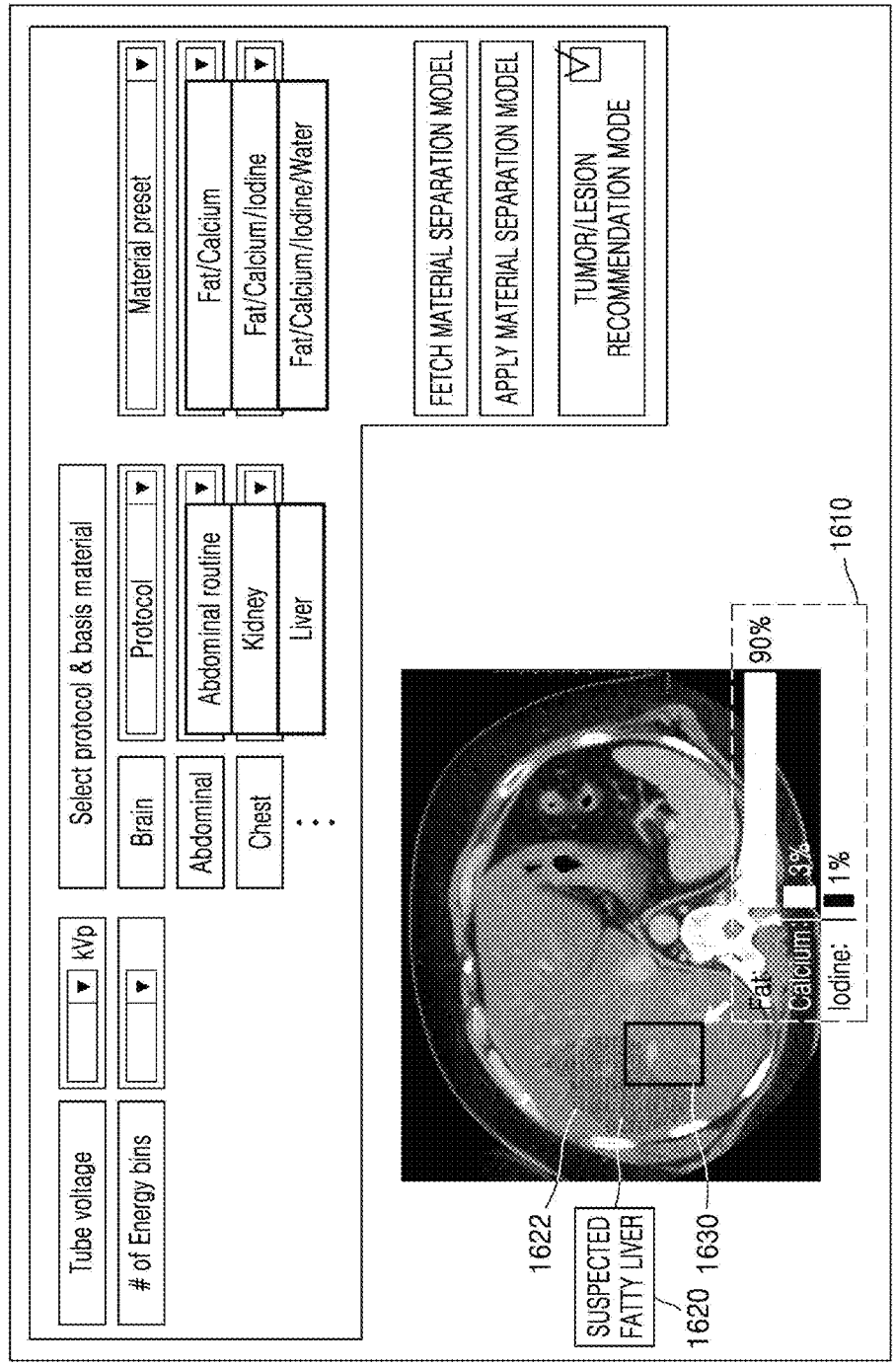
FIG. 16 illustrates a GUI view for displaying tumor/lesion information, according to an embodiment of the disclosure.

FIG. 16 illustrates a GUI view for displaying tumor/lesion information, according to an embodiment of the disclosure.

According to an embodiment of the disclosure, the tomographic image processing apparatus may extract a fatty liver suspicious region in an abdominal tomographic image of an object and provide disease information 1620 regarding the fatty liver suspicious region 1622. The fatty liver suspicious region 1622 may be extracted from the entire region of the object including a region other than an ROI 1630. The fatty liver suspicious region 1622 may be displayed in a pattern or color having a transparency applied thereto, and thus, structural information of the object in a tomographic image may be provided. Material separation information 1610 with respect to the selected ROI 1630 may be provided together with information about a disease or lesion.

Figure 17:
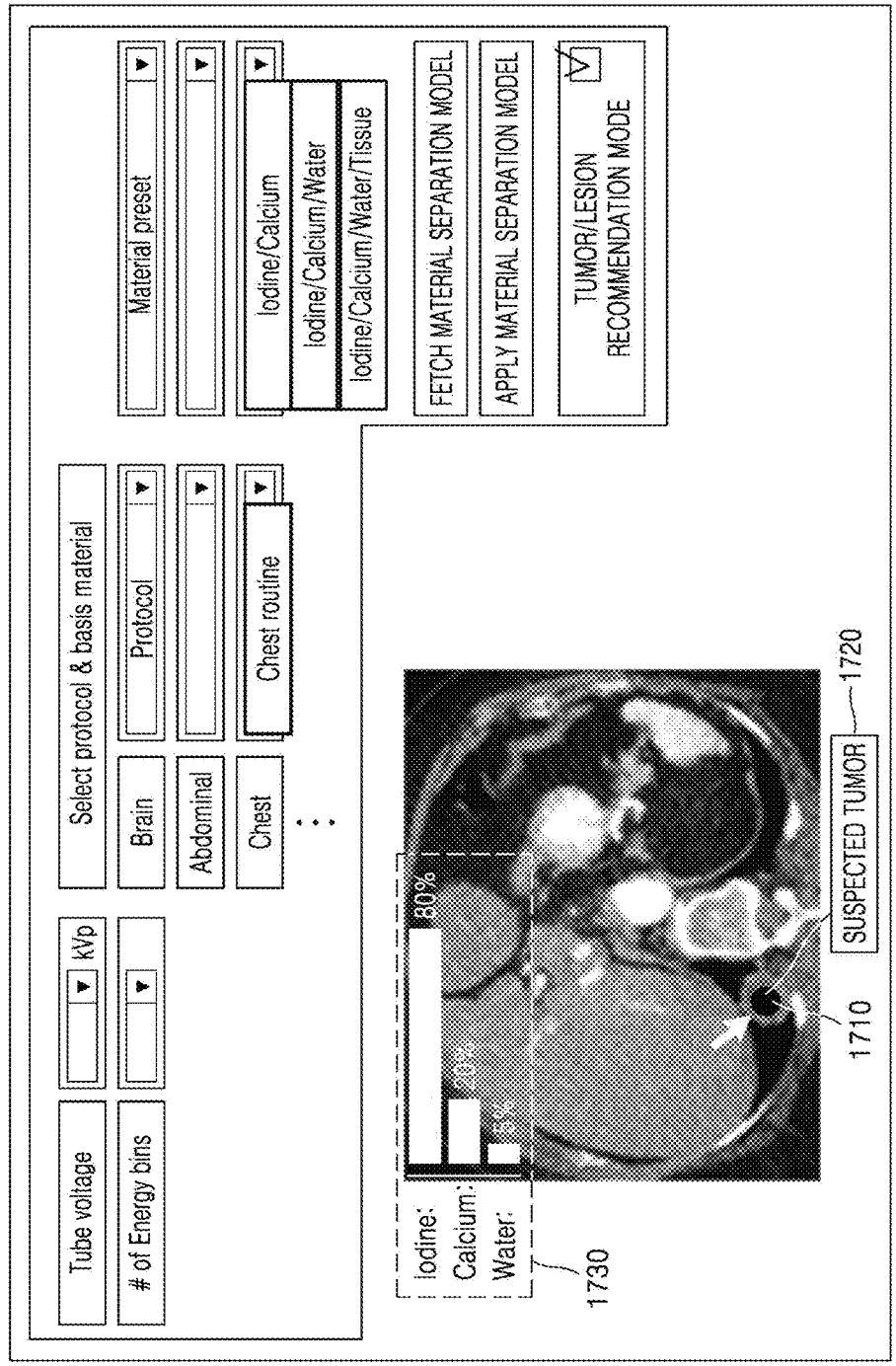
FIG. 17 illustrates a GUI view for displaying tumor/lesion information, according to an embodiment of the disclosure.

FIG. 17 illustrates a GUI view for displaying tumor/lesion information, according to an embodiment of the disclosure.

According to an embodiment of the disclosure, the tomographic image processing apparatus may extract a tumor suspicious region 1710 from a chest tomographic image and provide disease information 1720 regarding the tumor suspicious region 1710. When a selected ROI is determined to correspond to a disease or tumor, the tomographic image processing apparatus may provide information about the tumor suspicious region 1710 and the disease information 1720. Material separation information 1730 with respect to a selected ROI may be provided together with information about a disease or lesion.

Figure 18:
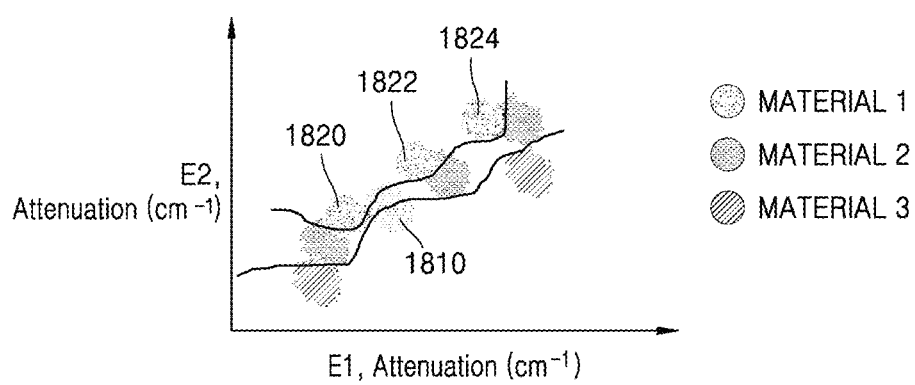
FIG. 18 is a diagram for explaining a material separation model according to an embodiment of the disclosure.

FIG. 18 is a diagram for explaining a material separation model according to an embodiment of the disclosure.

Materials included in an object have unique attenuation characteristics. The attenuation characteristics vary according to an energy level of X-rays. According to embodiments of the disclosure, material separation information for each pixel in a tomographic image is acquired based on spectral tomographic image data by using attenuation characteristics of a material that vary depending on an energy level. FIG. 18 is a graph showing attenuation characteristics of a plurality of materials at two energy levels. The abscissa and ordinate respectively represent linear attenuation coefficients ($cm^{-1}$) at energy levels E1 and E2. As shown in FIG. 18, materials 1 through 3 each exhibit different attenuation profiles at the energy levels E1 and E2. A plurality of data bundles for each of the materials 1 through 3 respectively correspond to different densities or concentrations. For example, there may be three data bundles 1820, 1822, and 1824 for material 1, and a density or concentration of the material 1 increases in the order of data bundle 1824 to data bundle 1822 to data bundle 1820. In general, as a density or concentration of a material becomes higher, its attenuation occurs to a greater extent. The material may be expressed in density or concentration according to its type. As described above, when attenuation data values for the materials 1 through 3 are arranged for each density or concentration in a first space where each axis corresponds to a different energy level, the first space is divided into smaller spaces for each material. When new data 1810 for a material of which the type is unknown is placed in the first space, material separation information indicating which material corresponds to the new data 1810 may be recognized. As a methodology for acquiring material separation information with this concept, embodiments of the disclosure propose a method of solving an equation representing a material separation model from a spectral tomographic image and a method using machine learning or deep learning.

Figure 19:
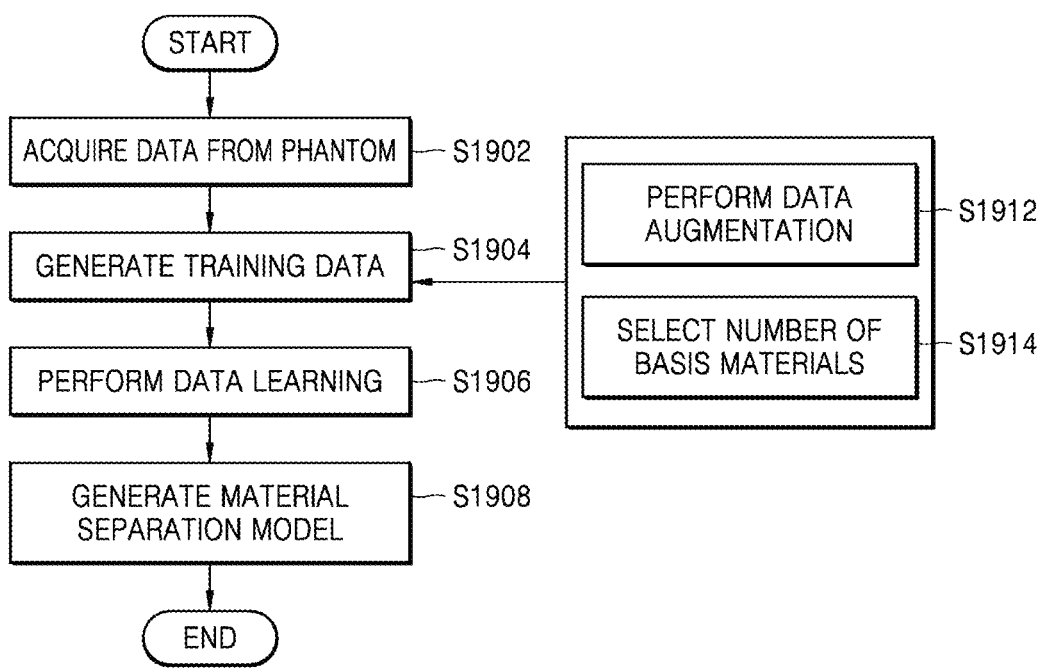
FIG. 19 is a flowchart of a method of generating a material separation model, according to an embodiment of the disclosure.

FIG. 19 is a flowchart of a method of generating a material separation model, according to an embodiment of the disclosure.

According to an embodiment of the disclosure, a tomographic image processing apparatus generates a material separation model by using training data acquired from a phantom. The training data acquired from the phantom is data acquired when the type and density or concentration of a material in each region of the object are pre-known. Thus, according to an embodiment of the disclosure, the material separation model may be generated using the training data acquired from the phantom.

Referring to FIG. 19, first, the tomographic image processing apparatus acquires training data from a phantom (S1902). The training data includes spectral tomographic image data acquired by scanning the phantom and material separation information and density/concentration information corresponding to each region of an object. In this case, the spectral tomographic image data represents attenuation information for each pixel, and material separation information indicates the type of a material in each pixel.

Then, the tomographic image processing apparatus generates training data by performing additional processing on the training data acquired from phantom. The additional processing on the training data may include data augmentation (S1912) and selection of the number of materials (S1914).

According to an embodiment of the disclosure, the tomographic image processing apparatus may increase the number of pieces of training data by applying a concentration/density augmentation model to the training data acquired from the phantom. When all training data are to be acquired for each concentration/density, this acquisition of training data causes an excessive load. Thus, according embodiments of the disclosure, the burden of acquiring training data may be significantly reduced by augmenting training data for each concentration/density based on information about a change in attenuation characteristics according to a pre-known concentration/density. Furthermore, the performance of training and accuracy of a material separation model to be acquired may be improved by increasing the number of pieces of training data via augmentation of the training data.

Furthermore, the tomographic image processing apparatus may select a range and number of pieces of training data to be used by selecting the number of basis materials (S1914). The number of energy levels required for training data and complexity of training vary depending on the number of basis materials. Thus, unnecessary training may be avoided by selecting the number of basis material during the additional processing of the training data.

The tomographic image processing apparatus performs data learning by using the training data generated via the additional processing (S1906). After performing the data learning, the tomographic image processing apparatus generates a material separation model (S1908).

Figure 20:
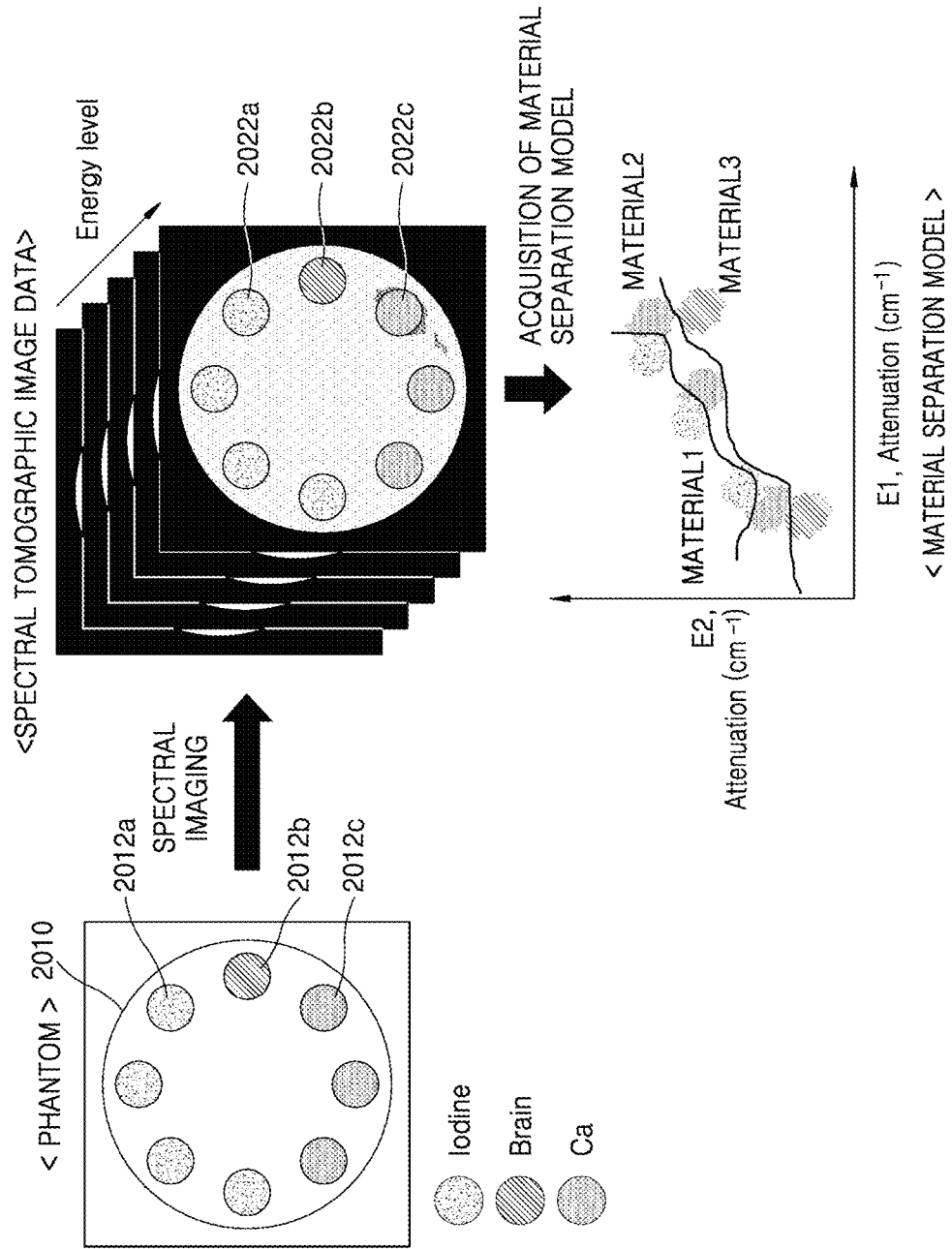
FIG. 20 illustrates a process of acquiring training data from a phantom and obtaining a material separation model, according to an embodiment of the disclosure.

FIG. 20 illustrates a process of acquiring training data from a phantom 2010 and obtaining a material separation model, according to an embodiment of the disclosure.

The phantom 2010 is an object manufactured by a designer with a desired material combination and shape. Thus, because the designer has known all details about the phantom 2010 such as material information, shape information, etc., it is possible to obtain desired parameter values or information from tomographic image data acquired for the phantom 2010.

According to an embodiment of the disclosure, the phantom 2010 may have a shape such that iodine, brain, and calcium are arranged in a predetermined region at a predetermined density or concentration. Furthermore, a specific material in the phantom 2010 may be arranged in different concentrations. For example, in the phantom 2010, four different concentration regions are arranged for iodine, and three different density regions are arranged for calcium.

The tomographic image processing apparatus performs spectral tomography imaging on the phantom 2010 at predetermined energy levels and with a predetermined number of energies. The spectral tomography imaging is performed to acquire a plurality of pieces of spectral tomographic image data at a plurality of energy levels. Because the designer has already known information about the phantom 2010, the designer may also be aware of which material corresponds to each region in the spectral tomographic image data. For example, the designer may recognize that regions 2022a, 2022b, and 2022c in the spectral tomographic image data respectively correspond to iodine, brain, and calcium because regions 2022a, 2022b, and 2022c respectively correspond to regions 2012a, 2012b, and 2012c of the phantom 2010.

The designer may obtain a material separation model by using the spectral tomographic image data acquired for the phantom 2010.

Figure 21:
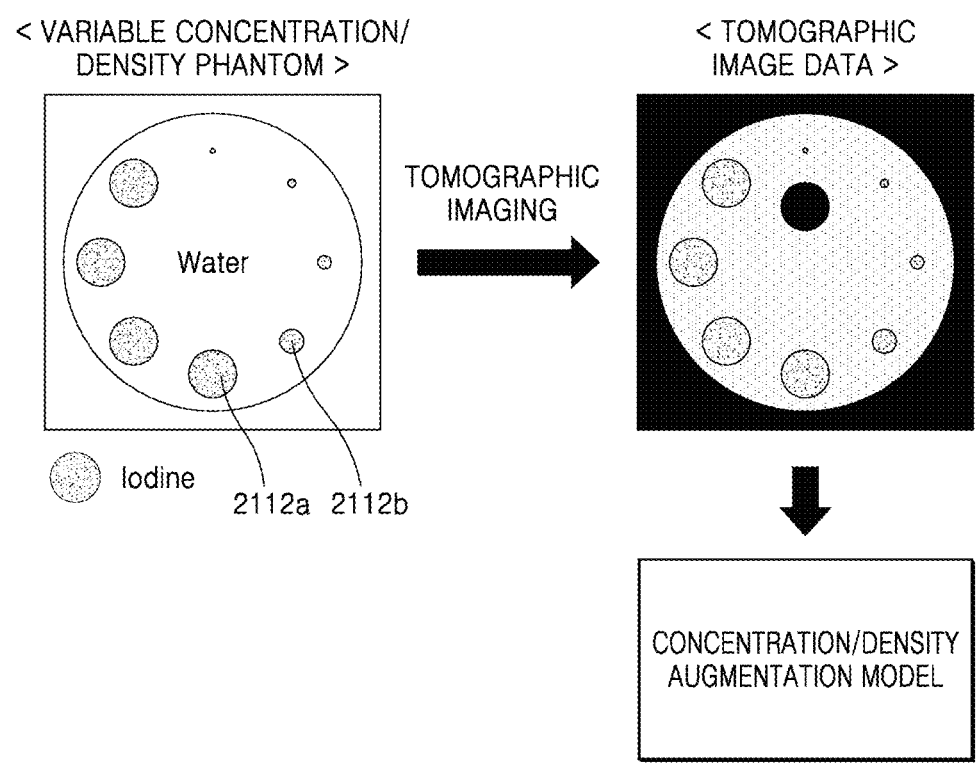
FIG. 21 is a diagram for explaining a process of obtaining a concentration/density augmentation model, according to an embodiment of the disclosure.

FIG. 21 is a diagram for explaining a process of obtaining a concentration/density augmentation model, according to an embodiment of the disclosure.

According to embodiments of the disclosure, a tomographic image processing apparatus augments training data by using information about energy attenuation profiles of each material that vary according to a concentration/density.

According to an embodiment of the disclosure, the tomographic image processing apparatus performs data augmentation by using an energy attenuation profile according to a pre-known concentration/density. For example, the tomographic image processing apparatus may perform data augmentation by fitting an attenuation coefficient for each concentration at each energy level.

According to another embodiment of the disclosure, the tomographic image processing apparatus obtains a concentration/density augmentation model by using a variable concentration/density phantom 2110 including target materials with different concentrations/densities. The variable concentration/density phantom 2110 includes a plurality of regions, each region including a target material with a different concentration/density. For example, the variable concentration/density phantom 2110 includes a plurality of regions respectively containing different concentrations of iodine. A region 2112a may have a higher concentration than a region 2112b. The tomographic image processing apparatus acquires tomographic image data by performing tomography imaging on the variable concentration/density phantom 2110. The variable concentration/density phantom 2110 may be scanned at a single energy or be subjected to spectral tomography imaging. The tomographic image processing apparatus may generate a concentration/density augmentation model by using tomographic image data acquired for the variable concentration/density phantom 2110. When the variable concentration/density phantom 2110 is scanned at a single energy level, the tomographic image processing apparatus may generate a concentration/density augmentation model at the single energy level and may perform data augmentation by applying the generated concentration/density augmentation model to other energy levels as well. When the variable concentration/density phantom 2110 is subjected to spectral tomography imaging at energy levels, the tomographic image processing apparatus may generate a concentration/density augmentation model at each of the energy levels.

Figure 22:
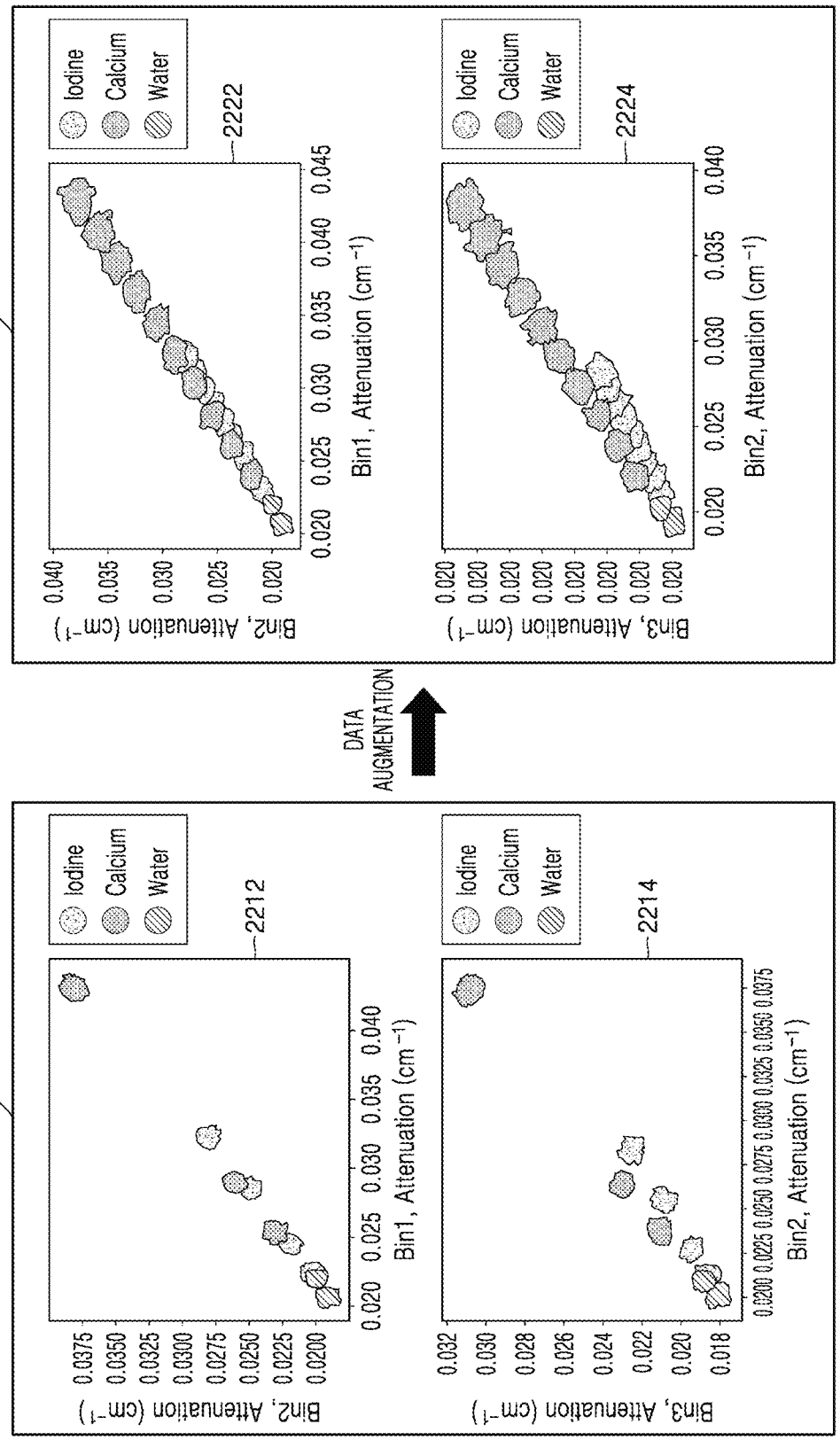
FIG. 22 is a diagram for explaining a data augmentation process, according to an embodiment of the disclosure.

FIG. 22 is a diagram for explaining a data augmentation process, according to an embodiment of the disclosure.

Data augmentation is performed by applying a concentration/density augmentation model to first training data 2210 acquired for a phantom. The training data acquired for the phantom is hereinafter called first training data 2210, and augmented training data is hereinafter called second training data 2220. The first training data 2210 represents attenuation information expressed in a space having at least two energy levels as its axes. For example, the first training data 2210 may include training data 2212 representing attenuation information at energy level 1 Bin1 and energy level 2 Bin2 and training data 2214 representing attenuation information at the energy level 2 Bin2 and energy level 3 Bin3. The first training data includes only attenuation information corresponding to a density/concentration of a material in the phantom.

The tomographic image processing apparatus generates the second training data 2220 by applying a concentration/density augmentation model to the first training data 2210. The second training data 2220 has an increased number of pieces of data by further including attenuation information corresponding to a concentration/density not represented in the first training data 2210. In this case, training data 2222 corresponds to the training data 2212 while training data 2224 corresponds to the training data 2214. As shown in FIG. 22, the second training data 2220 has a significantly increased number of data bundles compared to the first training data 2210. For example, the training data 2222 in the second training data 2220 corresponds to the training data 2212, and four concentrations of iodine are plotted in the training data 2212 while eight concentrations of iodine are plotted in the training data 2222. Furthermore, as the training data 2212 is transformed into the training data 2222, the number of densities of calcium increases from three (3) to nine (9). In this way, data augmentation may significantly increase the number of pieces of training data, thereby greatly improving the performance of a material separation model and reducing the load of generating training data.

Figure 23:
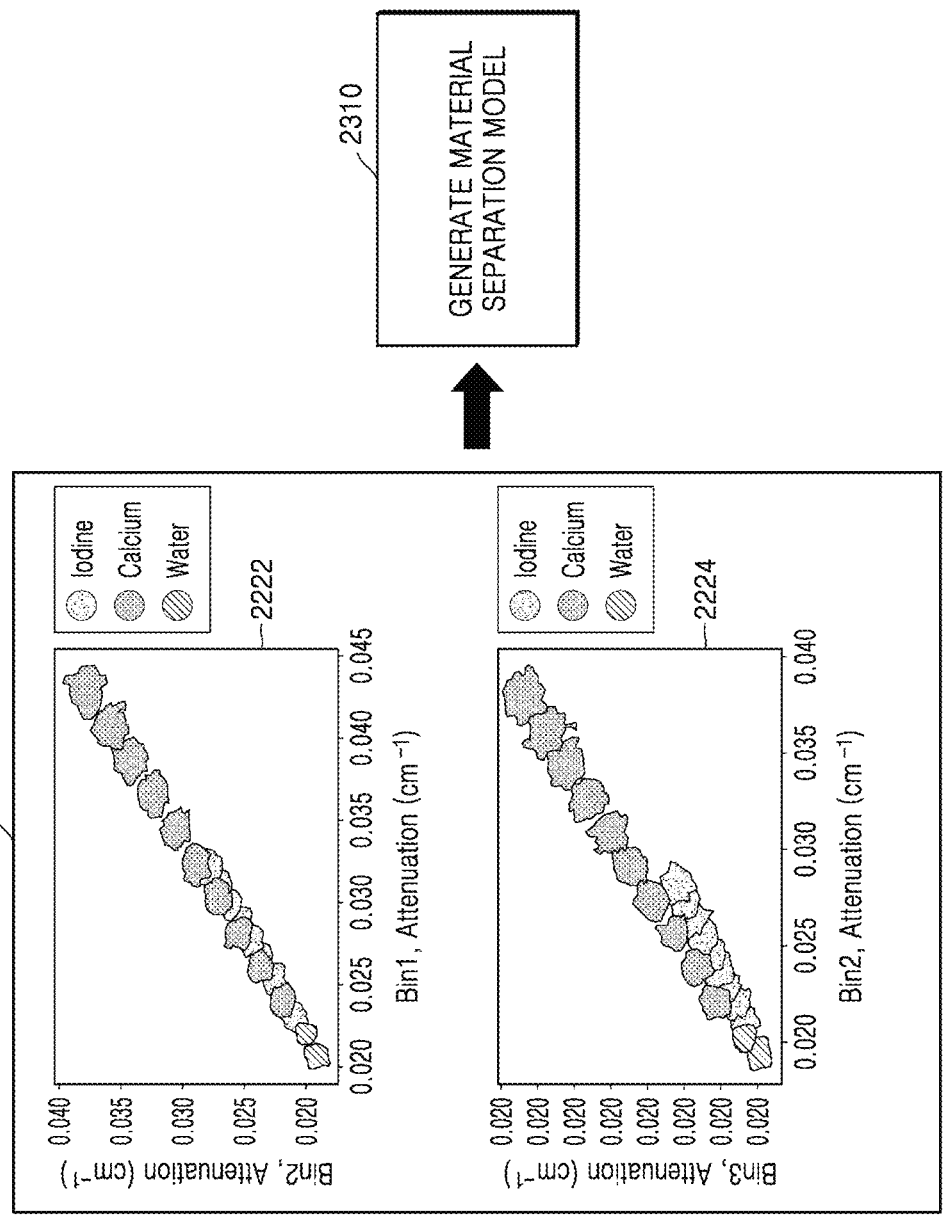
FIG. 23 illustrates a process of generating a material separation model based on second training data, according to an embodiment of the disclosure.

FIG. 23 illustrates a process of generating a material separation model based on second training data, according to an embodiment of the disclosure.

Referring to FIG. 23, a tomographic image processing apparatus generates a material separation model based on augmented second training data 2220 (2310).

According to an embodiment of the disclosure, the tomographic image processing apparatus may generate the material separation model by solving an equation for material separation. The material separation model may be represented by using Equation (1). A linear attenuation coefficient for each pixel may be defined by Equation (1):

$$\mu(E) = \sum_{i=1}^{n} f_i \mu_i(E), \text{ with } \sum_{i=1}^{n} f_i = 1 \quad (1)$$

where $\mu(E)$ is a linear attenuation coefficient at an energy level, $f_i$ is a probability of being an i-th material, and $\mu_i(E)$ is a linear attenuation coefficient of the i-th material at the energy level.

When linear attenuation coefficients are respectively obtained at N energy levels and a material separation model includes n materials, a linear attenuation coefficient at each energy level may be defined by Equation (2):

$$\mu(E_1) = \mu_1(E_1)f_1 = \mu_2(E_1)f_2 + \ldots + \mu_n(E_1)f_n \quad (2)$$
$$\mu(E_2) = \mu_1(E_2)f_1 = \mu_2(E_2)f_2 + \ldots + \mu_n(E_2)f_n$$
$$\vdots$$
$$\mu(E_N) = \mu_1(E_N)f_1 = \mu_2(E_N)f_2 + \ldots + \mu_n(E_N)f_n$$

By expressing Equation (2) in a matrix form, Equation (3) is obtained:

$$\begin{bmatrix} \mu(E_1) \\ \vdots \\ \mu(E_N) \end{bmatrix} = \begin{bmatrix} \mu_1(E_1) & \cdots & \mu_n(E_1) \\ \vdots & \ddots & \vdots \\ \mu_1(E_N) & \cdots & \mu_n(E_N) \end{bmatrix} \begin{bmatrix} f_1 \\ \vdots \\ f_n \end{bmatrix} \quad (3)$$

Because the material separation information to be obtained from an input tomographic image is a probability that each pixel corresponds to each material, the material separation information may be obtained by using Equation (4):

$$\begin{bmatrix} f_1 \\ \vdots \\ f_n \end{bmatrix} = inv\left(\begin{bmatrix} \mu_1(E_1) & \cdots & \mu_n(E_1) \\ \vdots & \ddots & \vdots \\ \mu_1(E_N) & \cdots & \mu_n(E_N) \end{bmatrix}\right)\begin{bmatrix} \mu(E_1) \\ \vdots \\ \mu(E_N) \end{bmatrix} \quad (4)$$

Eventually, to obtain the material separation information, a value of a matrix defined by Equation (5) needs to be known, and a material separation model is represented by the matrix of Equation (5):

$$\begin{bmatrix} \mu_1(E_1) & \cdots & \mu_n(E_1) \\ \vdots & \ddots & \vdots \\ \mu_1(E_N) & \cdots & \mu_n(E_N) \end{bmatrix} \quad (5)$$

According to an embodiment, the tomographic image processing apparatus may calculate the value of the matrix of Equation (5) by substituting into Equation (5) a value of a matrix on the left side of Equation (4) and a value of a second matrix on the right side thereof. According to the embodiment of the disclosure, spectral tomographic image data at a number of energy levels equal to the number of materials to be separated is required to generate the material separation model. According to an embodiment of the disclosure, it is possible to separate a greater number of materials than the number of energy levels by using machine learning or deep learning methods FIG. 24A is a block diagram of a configuration of a deep neural network (DNN) processor 2430, according to an embodiment of the disclosure.

According to an embodiment of the disclosure, a tomographic image processing apparatus may generate a material separation model based on training data via machine learning. For example, the material separation model may be generated using a DNN. To achieve this, the tomographic image processing apparatus may include a DNN processor or use a DNN processor provided in an external device. When the DNN processor is included in the tomographic image processing apparatus, it may be separate from or be included in the processor (320 of FIG. 3).

Figure 24A:
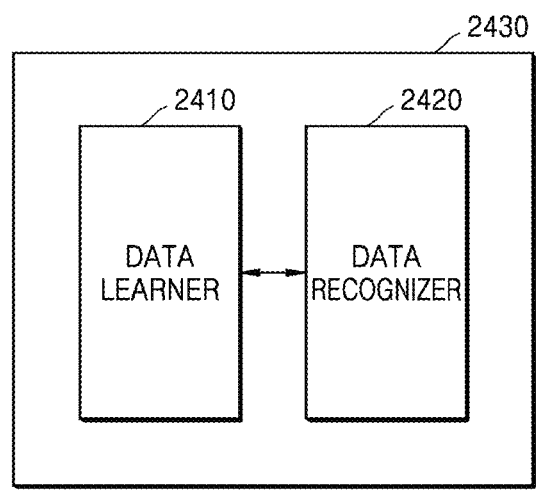
FIG. 24A is a block diagram of a configuration of a deep neural network (DNN) processor, according to an embodiment of the disclosure.

Referring to FIG. 24A, according to an embodiment of the disclosure, the DNN processor 2430 may include a data learner 2410 and a data recognizer 2420.

The data learner 2410 may learn criteria for performing computations via the above-described DNN. In detail, the data learner 2410 may learn criteria with respect to which data will be used to predict a material separation model, how to determine a situation by using data, etc. The data learner 2410 may acquire data to be used for training and learn criteria for generating material separation information by applying the acquired data to a data recognition model as will be described below. In this case, data used by the data learner 2410 for training may be second training data that are subjected to data augmentation. In detail, an attenuation coefficient at each pixel, a material type, concentration/density information in the second training data may be input to the data learner 2410. In this case, an attenuation coefficient at each pixel may correspond to raw data for each pixel.

The data recognizer 2420 may determine a situation based on data. The data recognizer 2420 may identify material separation information in an input tomographic image by using the trained data recognition model such as a first artificial cultured neural network.

In detail, the data recognizer 2420 may acquire predetermined data according to the learned preset criteria and determine a specific situation based on the predetermined data by using a data recognition model that takes the acquired data as an input value Furthermore, a resultant value output by the data recognition model that takes the acquired data as an input value may be used to modify and refine the data recognition model.

According to an embodiment of the disclosure, the data recognition model constructed by the data recognizer 2420, such as the first artificial cultured neural network generated by training a DNN (2520 of FIG. 25), or a second artificial cultured neural network generated by training the first artificial cultured neural network, may be built to infer material separation information from an input tomographic image by learning a plurality of training data.

In detail, the data recognizer 2420 may receive a value of each pixel in spectral tomographic image data (i.e., raw data) and output material separation information indicating a probability that each pixel corresponds to a specific material. The data recognizer 2420 may be further modeled to generate the material separation information according to a material combination.

At least one of the data learner 2410 or the data recognizer 2420 may be fabricated in the form of at least one hardware chip that may be mounted in the tomographic image processing apparatus. For example, at least one of the data learner 2410 or the data recognizer 2420 may be manufactured in the form of a dedicated hardware chip for AI, or as part of an existing general-purpose processor (e.g., a central processing unit (CPU) or application processor) or dedicated graphics processor (e.g., a graphical processing unit (GPU)) and be mounted in the tomographic image processing apparatus.

Furthermore, the data learner 2410 and the data recognizer 2420 may be respectively mounted in the tomographic image processing apparatus (300a of FIG. 3 or 300b of FIG. 4) and an external device. For example, one of the data learner 2410 and the data recognizer 2420 may be included in the tomographic image processing apparatus 300a or 300b while the other one may be included in a server. Furthermore, the data learner 2410 and the data recognizer 2420 are connected to each other by wire or wirelessly, such that model information generated by the data learner 2410 may be provided to the data recognizer 2420, and data input to the data recognizer 2420 may be provided to the data learner 2410 as additional training data.

In addition, at least one of the data learner 2410 or the data recognizer 2420 may be implemented as a software module. When the at least one of the data learner 2410 or the data recognizer 2420 is implemented as a software module (or a program module including instructions), the software module may be stored in non-transitory computer readable recording media. Furthermore, in this case, at least one software module may be provided by an operating system (OS) or predetermined application. Alternatively, some of the at least one software module may be provided by the OS while the rest thereof may be provided by the predetermined application.

Figure 24B:
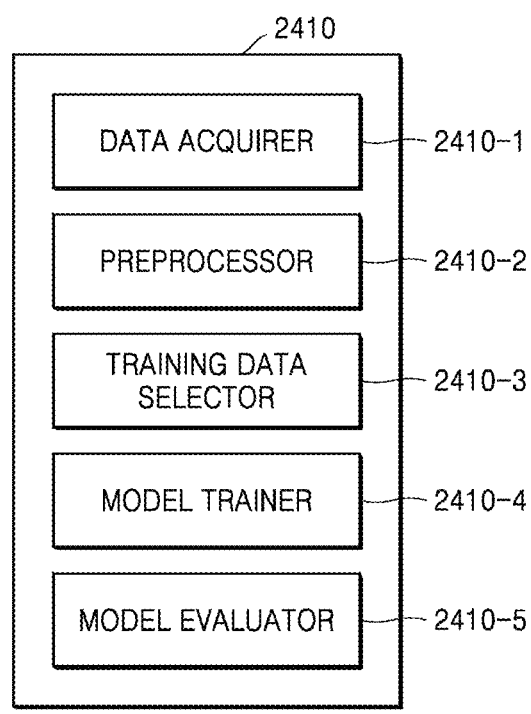
FIG. 24B is a block diagram of a configuration of a data learner included in a DNN processor, according to an embodiment of the disclosure.

FIG. 24B is a block diagram of a configuration of a data learner 2410 included in a DNN processor, according to an embodiment of the disclosure.

Referring to FIG. 24B, according to some embodiments of the disclosure, the data learner 2410 may include a data acquirer 2410-1, a preprocessor 2410-2, a training data selector 2410-3, a model trainer 2410-4, and a model evaluator 2410-5.

The data acquirer 2410-1 acquires training data. The data acquirer 2410-1 may acquire training data from a predetermined database (DB) for storing training data.

The preprocessor 2410-2 may preprocess the acquired training data such that the acquired training data may be used in training for determination of a situation. According to an embodiment of the disclosure, the preprocessor 2410-2 may process the acquired training data into a preset format such that the model trainer 2410-4 to be described later may use spectral tomographic image data that is data acquired for training for determination of a situation.

The training data selector 2410-3 may select data necessary for training from among the preprocessed data. The selected data may be provided to the model trainer 2410-4. The training data selector 2410-3 may select data necessary for training from among the preprocessed data according to preset criteria for determination of a situation. Furthermore, the training data selection unit 1230 may select data according to preset criteria learned by the model trainer 2410-4 to be described later.

The model trainer 2410-4 may learn a criterion with respect to how to determine a situation based on training data. Furthermore, the model trainer 2410-4 may learn a criterion with respect to which training data is to be used for determination of a situation.

According to an embodiment of the disclosure, the model trainer 2410-4 may learn a plurality of pieces of spectral tomographic image data and train a material separation model based on the learned pieces of spectral tomographic image data.

Furthermore, the model trainer 2410-4 may use training data to train a data recognition model used for determining a situation. In this case, the data recognition model may be a previously generated model.

The data recognition model may be built by taking into account an application field of the data recognition model, an objective of learning, or a computer performance of a device. For example, the data recognition model may be a model based on a neural network. Models such as DNN, recurrent neural network (RNN), and bidirectional recurrent deep neural network (BRDNN) may be used as the data recognition model, but are limited thereto.

Furthermore, after the data recognition model is trained, the model trainer 2410-4 may store the trained data recognition model. In this case, the model trainer 2410-4 may store the trained data recognition model in a memory of an electronic device including the data recognizer (2420 of FIG. 24A) According to another embodiment of the disclosure, the model trainer 2410-4 may store the trained data recognition model in a memory of an electronic device including a data recognizer 2420 of FIG. 24C as will be described below. Alternatively, the model trainer 2410-4 may store the trained data recognition model in a memory of a server connected to the electronic device via a wired or wireless network.

In this case, for example, the memory in which the first artificial cultured neural network that is the trained data recognition model is stored may store together a command or data related to at least one component of the electronic device. Furthermore, the memory may also store software and/or programs. For example, the programs may include kernel, middleware, application programming interface (API) and/or application program (or "application").

The model evaluator 2410-5 inputs evaluation data to the data recognition model, and may cause the model trainer 2410-4 to train again the data recognition model when a recognition result obtained from the evaluation data does not satisfy predetermined accuracy or reliability that is a predetermined criterion. In this case, the evaluation data may be preset data for evaluating the data recognition model.

For example, when the number or ratio of pieces of evaluation data with respect to which recognition results are not accurate from among recognition results output from the trained data recognition model with respect to evaluation data exceeds a preset threshold, the model evaluator 2410-5 may evaluate that a predetermined criterion is not satisfied. For example, when the predetermined criterion is defined as a ratio of 2%, and when the trained data recognition model outputs wrong recognition results with respect to more than 20 pieces of evaluation data among a total of 1000 pieces of evaluation data, the model evaluator 2410-5 may evaluate the trained data recognition model as not being suitable.

A least one of the preprocessor 2410-2, the training data selector 2410-3, the model trainer 2410-4, or the model evaluator 2410-5 in the data learner 2410 may be fabricated in the form of at least one hardware chip that may be mounted in the tomographic image processing apparatus or an external device.

Furthermore, the preprocessor 2410-2, the training data selector 2410-3, the model trainer 2410-4, and the model evaluator 2410-5 may be mounted in one electronic device, or be respectively mounted in different electronic devices. For example, some of the preprocessor 2410-2, the training data selector 2410-3, the model trainer 2410-4, and the model evaluator 2410-5 may be included in the tomographic image processing apparatus while the rest thereof may be included in a server.

Figure 24C:
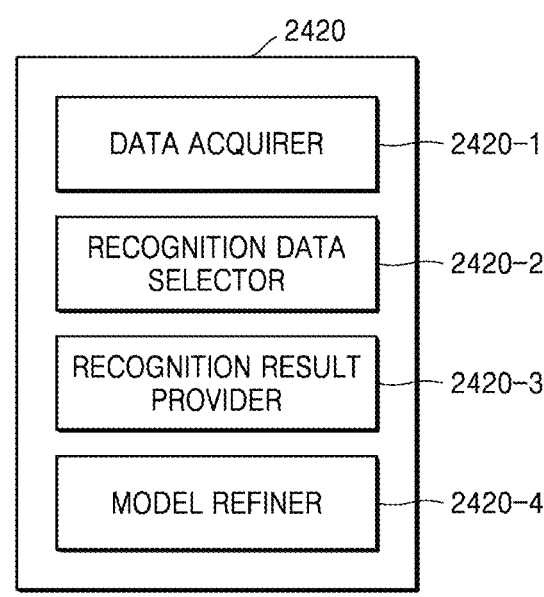
FIG. 24C is a block diagram of a configuration of a data recognizer in a DNN processor, according to an embodiment of the disclosure.

FIG. 24C is a block diagram of a configuration of a data recognizer 2420 in a DNN processor, according to an embodiment of the disclosure.

Referring to FIG. 24C, according to some embodiments of the disclosure, the data recognizer 2420 may include a preprocessor 2420-1, a recognition data selector 2420-2, a recognition result provider 2420-3, and a model refiner 2420-4.

The preprocessor 2420-1 may preprocess the acquired input data such that the acquired input data may be used for data recognition. The preprocessor 2420-1 may process the acquired input data into a preset format such that the recognition result provider 2420-3 to be described below may use the acquired input data for determining a situation.

The recognition data selector 2420-2 may select data necessary for data recognition from among the preprocessed data. The selected data may be provided to the recognition result provider 2420-3. The recognition data selector 2420-2 may select some or all of the preprocessed data according to preset criteria for data recognition. Furthermore, the recognition data selector 2420-2 may select data according to preset criteria learned by the model trainer (2410-4 of FIG. 24B).

The recognition result provider 2420-3 may determine a situation by applying the selected data to a data recognition model. The recognition result provider 2420-3 may provide a recognition result according to the purpose of data recognition.

The model refiner 2420-4 may modify and refine the data recognition model based on evaluation of the recognition result provided by the recognition result provider 2420-5. For example, the model refiner 2420-4 may cause the model trainer 2410-4 to modify and refine the data recognition model by providing the recognition result from the recognition result provider 2420-3 to the model trainer 2410-4.

According to an embodiment of the disclosure, each time an input tomographic image is additionally obtained, the model refiner 2420-4 may modify and refine the first artificial cultured neural network by training the first artificial cultured neural network as the data recognition model. Furthermore, the model refiner 2420-4 may modify or refine the first artificial cultured neural network and acquire a second artificial cultured neural network by training the first artificial cultured neural network with at least one second medical image, which is obtained by performing computations via the first artificial cultured neural network.

At least one of the preprocessor 2420-1, the recognition data selector 2420-2, the recognition result provider 2420-3, or the model refiner 2420-4 included in the data recognizer 2420 may be fabricated in the form of at least one hardware chip and mounted in the electronic device. Furthermore, the preprocessor 2420-1, the recognition data selector 2420-2, the recognition result provider 2420-3, and the model refiner 2420-4 may be mounted in one electronic device, or be respectively mounted in different electronic devices. For example, some of the preprocessor 2420-1, the recognition data selector 2420-2, the recognition result provider 2420-3, and the model refiner 2420-4 may be included in the electronic device while the rest thereof may be included in a server.

Figure 25:
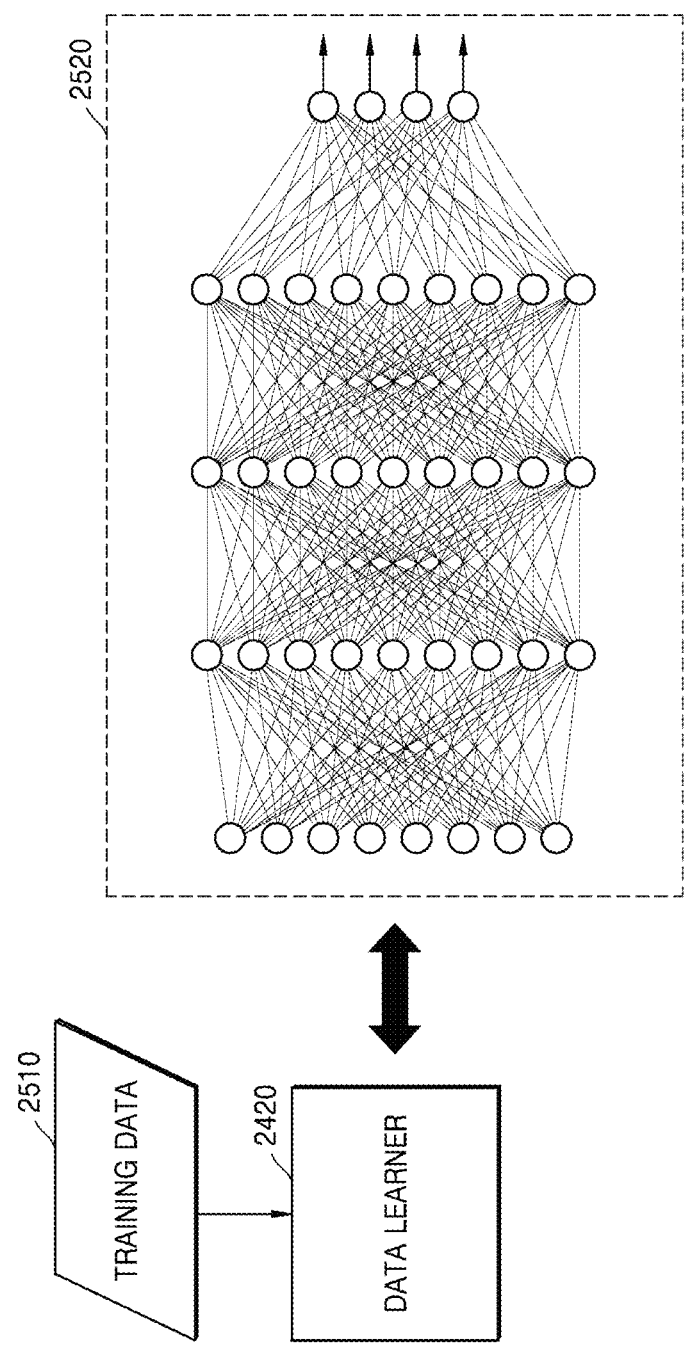
FIG. 25 illustrates a process of training a material separation model, according to an embodiment of the disclosure.

FIG. 25 illustrates a process of training a material separation model, according to an embodiment of the disclosure.

According to an embodiment of the disclosure, the material separation model may be trained using the DNN processors described with reference to FIGS. 24A through 24C. The data learner 2410 may acquire training data 2510 and train a DNN 2520 with the training data 2510. For example, the training data 2510 may be second training data that are subjected to data augmentation. The DNN 2520 may generate layers and nodes in each layer via training and determine a weight from node to node and a material separation model.

According to another embodiment of the disclosure, the training data 2510 may include at least one of a material combination, a scanning protocol, an energy level of a spectral tomographic image, or the number of energy levels, or a combination thereof.

Figure 26:
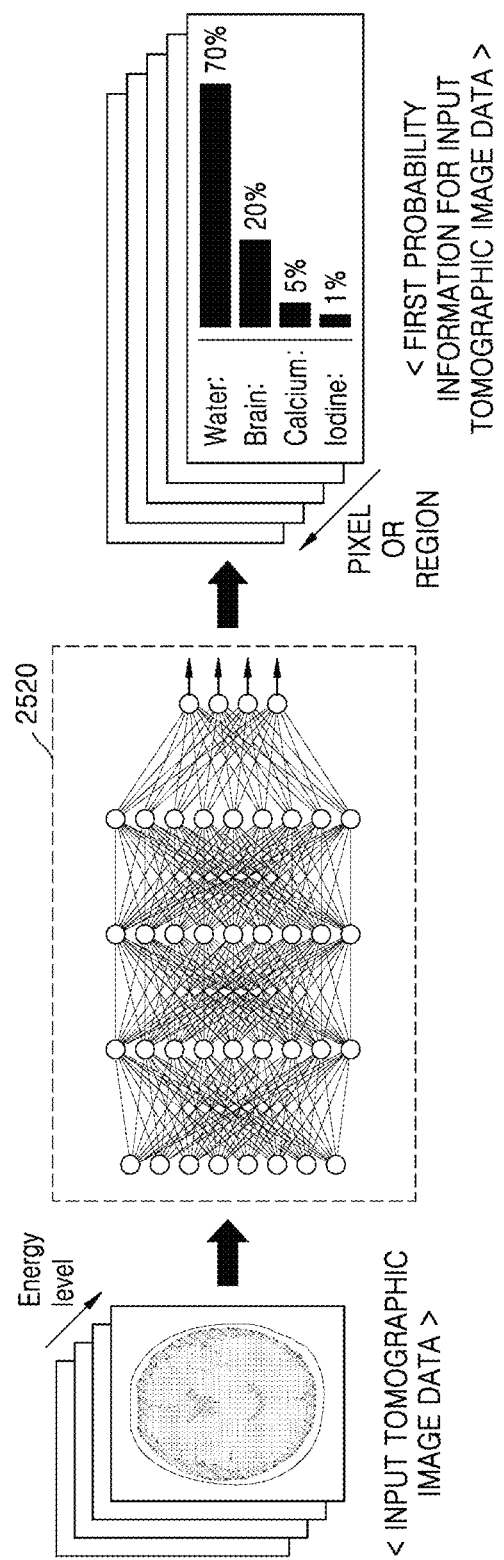
FIG. 26 illustrates a process of recognizing data by using a material separation model, according to an embodiment of the disclosure.

FIG. 26 illustrates a process of recognizing data by using a material separation model, according to an embodiment of the disclosure.

According to an embodiment of the disclosure, the material separation model may include a DNN 2520 trained by the data learner (2420 of FIG. 25). When spectral tomographic image data is input to the trained DNN 2520, material separation information with respect to each pixel or unit region may be output from the DNN 2520. At least one of a material combination, a scanning protocol, an energy level of a spectral tomographic image, or the number of energy levels, or a combination thereof may be additionally input to the DNN 2520.

According to an embodiment of the disclosure, a tomographic image processing apparatus may generate a material separation model and acquire material separation information by using machine learning and a DNN, thereby improving the accuracy of the material separation model.

The embodiments may be implemented as a software program including instructions stored in a computer-readable storage medium.

A computer may refer to a device configured to retrieve an instruction stored in the computer-readable storage medium and to operate, in response to the retrieved instruction, and may include an tomographic imaging apparatus according to embodiments.

The computer-readable storage medium may be provided in the form of a non-transitory storage medium. In this regard, the term 'non-transitory' means that the storage medium does not include a signal and is tangible, and the term does not distinguish between data that is semi-permanently stored and data that is temporarily stored in the storage medium.

In addition, the tomographic imaging apparatus or the method of controlling the tomographic imaging apparatus according to embodiments may be provided in the form of a computer program product. The computer program product may be traded, as a product, between a seller and a buyer.

The computer program product may include a software program and a computer-readable storage medium having stored thereon the software program. For example, the computer program product may include a product (e.g. a downloadable application) in the form of a software program electronically distributed by a manufacturer of the tomographic imaging apparatus or through an electronic market (e.g., Google™, Play Store™, and App Store™). For such electronic distribution, at least a part of the software program may be stored on the storage medium or may be temporarily generated. In this case, the storage medium may be a storage medium of a server of the manufacturer, a server of the electronic market, or a relay server for temporarily storing the software program.

In a system consisting of a server and a terminal (e.g., the tomographic imaging apparatus), the computer program product may include a storage medium of the server or a storage medium of the terminal. Alternatively, in a case where a third device (e.g., a smartphone) that communicates with the server or the terminal is present, the computer program product may include a storage medium of the third device. Alternatively, the computer program product may include a software program that is transmitted from the server to the terminal or the third device or that is transmitted from the third device to the terminal.

In certain embodiments according to this disclosure, one of the server, the terminal, and the third device may execute the computer program product, thereby performing the method according to embodiments. Alternatively, at least two of the server, the terminal, and the third device may execute the computer program product, thereby performing the method according to embodiments in a distributed manner.

For example, the server (e.g., a cloud server, an artificial intelligence (AI) server, or the like) may execute the computer program product stored in the server, and may control the terminal to perform the method according to embodiments, the terminal communicating with the server.

As another example, the third device may execute the computer program product, and may control the terminal to perform the method according to embodiments, the terminal communicating with the third device. In more detail, the third device may remotely control the tomographic imaging apparatus to emit X-ray to an object, and to generate an image of an inner part of the object, based on detected radiation which passes the object and is detected in an X-ray detector.

As another example, the third device may execute the computer program product, and may directly perform the method according to embodiments, based on at least one value input from an auxiliary device (e.g., a gantry of CT system). In more detail, the auxiliary device may emit X-ray to an object and may obtain information of radiation which passes the object and is detected in an X-ray detector. The third device may receive an input of signal information about the detected radiation from the auxiliary device, and may generate an image of an inner part of the object, based on the input radiation information.

In a case where the third device executes the computer program product, the third device may download the computer program product from the server, and may execute the downloaded computer program product. Alternatively, the third device may execute the computer program product that is pre-loaded therein, and may perform the method according to the embodiments.

According to embodiments of the disclosure, diagnostic efficiency and accuracy may be increased by separating a material of an object in a spectral tomographic image and providing a result of the separation via a UI.

Furthermore, according to embodiments of the disclosure, a diagnosis by a user may be facilitated by estimating a predictable tumor or lesion based on a result of material separation in a spectral tomographic image and providing information about the tumor or lesion.

Furthermore, according to embodiments of the disclosure, accuracy of material separation may be improved by training a material separation model via machine learning and using the trained material separation model.

In addition, according to embodiments of the disclosure, the burden of collecting training data may be reduced and performance of training may be increased by increasing the number of pieces of training data via data augmentation.

While embodiments of the disclosure have been particularly shown and described with reference to the accompanying drawings, it will be understood by those of ordinary skill in the art that various changes in form and details may be made therein without departing from the spirit and scope of the disclosure as defined by the appended claims. The disclosed embodiments should be considered in descriptive sense only and not for purposes of limitation.

What is claimed is:

1. A tomographic image processing apparatus comprising:
   a display;
   an input device configured to receive an external input from an external device;
   a storage storing an input tomographic image of an object; and
   at least one processor configured to:
      control the display to display the input tomographic image;
      determine a material combination to be separated from the input tomographic image; and
      control the display to display material separation information corresponding to the determined material combination for a region of interest selected in the input tomographic image based on the external input
   wherein the input tomographic image is a spectral tomographic image comprising a plurality of tomographic images respectively corresponding to a plurality of energy levels, and
   the at least one processor is further configured to:
      obtain a material separation model for acquiring the material separation information based on the input tomographic image data of the input tomographic image by using training data which includes a plurality of pieces of spectral tomographic image data and is acquired when information about a proportion of each material and its energy attenuation value are known; and
      generate augmented training data by fitting a concentration or density to the training data.

2. The tomographic image processing apparatus of claim 1, wherein the at least one processor is further configured to select the material combination based on a type of the object or the external input.

3. The tomographic image processing apparatus of claim 1,
   wherein the storage further stores the material separation information for each pixel in the input tomographic image, and
   wherein the at least one processor is further configured to control the display to display the stored material separation information based on the external input for selecting the region of interest.

4. The tomographic image processing apparatus of claim 1, wherein the at least one processor is further configured to control the display to display information about a tumor or lesion in the input tomographic image of the object.

5. The tomographic image processing apparatus of claim 4, wherein the at least one processor is further configured to determine the information about the tumor or lesion based on the material separation information.

6. The tomographic image processing apparatus of claim wherein the at least one processor is further configured to:
    train a deep neural network with the augmented training data;
    generate a deep neural network model for differentiating the material separation information with respect to each pixel from the input tomographic image data of the input tomographic image; and
    identify the material separation information in the input tomographic image data by using the deep neural network model.

7. The tomographic image processing apparatus of claim 6, wherein the input tomographic image data is raw data of the input tomographic image.

8. The tomographic image processing apparatus of claim 1, wherein the region of interest is a region including at least one pixel.

9. The tomographic image processing apparatus of claim 1, wherein the material separation information is displayed in a graph form indicating probability information regarding the determined material combination.

10. The tomographic image processing apparatus of claim 1, wherein the material separation information is displayed in the input tomographic image as a color map representing a distribution of each material in the determined material combination.

11. The tomographic image processing apparatus of claim 1, further comprising a data acquirer configured to acquire raw data with respect to the object.

12. A tomographic image processing method comprising:
    displaying an input tomographic image of an object;
    determining a material combination to be separated from the input tomographic image;
    obtaining a material separation model for acquiring the material separation information based on the input tomographic image data of the input tomographic image by using training data which includes a plurality of pieces of spectral tomographic image data and is acquired when information about a proportion of each material and its energy attenuation value are known;
    generating augmented training data by fitting a concentration or density to the training data; and
        displaying material separation information corresponding to the determined material combination for a region of interest selected in the input tomographic image based on an external input,
    wherein the input tomographic image is a spectral tomographic image comprising a plurality of tomographic images respectively corresponding to a plurality of energy levels.

13. The tomographic image processing method of claim 12, wherein the determining of the material combination comprises selecting the material combination based on a type of the object or the external input.

14. The tomographic image processing method of claim 12, further comprising:
    storing the material separation information for each pixel in the input tomographic image; and
    displaying the stored material separation information based on the external input for selecting the region of interest.

15. The tomographic image processing method of claim 12, further comprising displaying information about a tumor or lesion in the input tomographic image of the object.

16. The tomographic image processing method of claim 15, further comprising determining the information about the tumor or lesion based on the material separation information.

17. The tomographic image processing method of claim 12, further comprising obtaining a material separation model for acquiring the material separation information based on input tomographic image data of the input tomographic image by using training data which includes a plurality of pieces of spectral tomographic image data and is acquired when information about a proportion of each material and its energy attenuation value are known.

18. A non-transitory computer recording medium having stored therein program commands, when executed by a processor, cause the processor to perform a tomographic image processing method comprising:
    displaying an input tomographic image of an object;
    determining a material combination to be separated from the input tomographic image;
    obtaining a material separation model for acquiring the material separation information based on the input tomographic image data of the input tomographic image by using training data which includes a plurality of pieces of spectral tomographic image data and is acquired when information about a proportion of each material and its energy attenuation value are known;
    generating augmented training data by fitting a concentration or density to the training data; and
        displaying material separation information corresponding to the determined material combination for a region of interest selected in the input tomographic image based on an external input,
    wherein the input tomographic image is a spectral tomographic image comprising a plurality of tomographic images respectively corresponding to a plurality of energy levels.

* * * * *